(12) United States Patent
Billington

(10) Patent No.: US 9,161,994 B1
(45) Date of Patent: Oct. 20, 2015

(54) COST MODEL ANALYSIS AND BREAKDOWN FOR COST BUILDUP

(75) Inventor: Corey A. Billington, San Jose, CA (US)

(73) Assignee: Deem, Inc., San Francisco, CA (US)

( * ) Notice: Subject to any disclaimer, the term of this patent is extended or adjusted under 35 U.S.C. 154(b) by 1014 days.

(21) Appl. No.: 11/093,615

(22) Filed: Mar. 29, 2005

(51) Int. Cl.
  *G06Q 10/00* (2012.01)
  *G06F 17/00* (2006.01)
  *A61K 48/00* (2006.01)

(52) U.S. Cl.
  CPC ...................................... *A61K 48/00* (2013.01)

(58) Field of Classification Search
  USPC .......................................................... 705/28
  See application file for complete search history.

(56) References Cited

U.S. PATENT DOCUMENTS

| | | | |
|---|---|---|---|
| 5,021,953 A | 6/1991 | Webber et al. | |
| 5,191,523 A | 3/1993 | Whitesage | |
| 5,237,499 A | 8/1993 | Garback | |
| 5,319,542 A | 6/1994 | King et al. | |
| 5,331,546 A | 7/1994 | Webber et al. | |
| 5,333,181 A | 7/1994 | Biggs | |
| 5,475,740 A | 12/1995 | Biggs et al. | |
| 5,570,283 A | 10/1996 | Shoolery et al. | |
| 5,655,008 A | 8/1997 | Futch et al. | |
| 5,732,398 A * | 3/1998 | Tagawa | 705/5 |
| 5,799,286 A | 8/1998 | Morgan et al. | |
| 5,819,092 A | 10/1998 | Ferguson et al. | |
| 5,832,451 A * | 11/1998 | Flake et al. | 705/5 |
| 5,832,453 A | 11/1998 | O'Brien | |
| 5,839,114 A * | 11/1998 | Lynch et al. | 705/5 |
| 5,842,178 A * | 11/1998 | Giovannoli | 705/26.4 |
| 5,852,812 A | 12/1998 | Reeder | |
| 5,870,721 A | 2/1999 | Norris | |
| 5,893,077 A | 4/1999 | Griffin | |
| 5,897,620 A | 4/1999 | Walker et al. | |
| 5,948,040 A | 9/1999 | DeLorme et al. | |
| 5,987,425 A * | 11/1999 | Hartman et al. | 705/20 |
| 5,991,742 A | 11/1999 | Tran | |
| 6,009,408 A | 12/1999 | Buchanan | |
| 6,018,715 A | 1/2000 | Lynch et al. | |
| 6,023,679 A * | 2/2000 | Acebo et al. | 705/5 |
| 6,029,144 A | 2/2000 | Barrett et al. | |
| 6,058,375 A | 5/2000 | Park | |

(Continued)

FOREIGN PATENT DOCUMENTS

CA      2291463      6/2001

OTHER PUBLICATIONS

Aggarwal, Gautam et al., U.S. Appl. No. 11/319,911, entitled "Method and System for Ranking Services on a Variable Scale of Compliance," filed Dec. 27, 2005.
Forshaw, David et al., U.S. Appl. No. 11/324,083, entitled "Method and System to Provide Cumulative Budget and Probabilites for a Return on Expenditure for Policy Enforcement," filed Dec. 29, 2005.
Gertsbakh, Ilya et al., "Periodic transportation schedules with flexible departure time: An interactive approach based on the periodic event scheduling program and the deficit function approach," European Journal of Operational Research, Feb. 15, 1991, pp. 298-309 (abstract only).

(Continued)

*Primary Examiner* — Ashford S Hayles
(74) *Attorney, Agent, or Firm* — Greenberg Traurig, LLP

(57) ABSTRACT

One embodiment of the invention includes a method and system to obtain data for fees and surcharges charged by multiple providers for multiple services based on prior interactions with the service providers, and provide an estimate for fees and surcharges to be charged by one of the service providers for one of the services based on the prior interactions with the service providers. In one embodiment, the fee data is extracted from one of electronic publishing of fees, billings for services rendered, and employee expense reports. In one embodiment, the estimated fees and surcharges include restricted access to a first subset of data to a first predetermined group.

20 Claims, 16 Drawing Sheets

(56) References Cited

U.S. PATENT DOCUMENTS

| | | | |
|---|---|---|---|
| 6,070,798 A | 6/2000 | Nethery | |
| 6,119,094 A * | 9/2000 | Lynch et al. | 705/5 |
| 6,195,420 B1 | 2/2001 | Tognazzini | |
| 6,230,204 B1 | 5/2001 | Fleming | |
| 6,295,521 B1 | 9/2001 | DeMarcken et al. | |
| 6,304,850 B1 | 10/2001 | Keller et al. | |
| 6,377,932 B1 * | 4/2002 | DeMarcken | 705/5 |
| 6,411,940 B1 | 6/2002 | Egendorf | |
| 6,435,406 B1 | 8/2002 | Pentel | |
| 6,442,526 B1 | 8/2002 | Vance et al. | |
| 6,477,520 B1 | 11/2002 | Malaviya et al. | |
| 6,553,346 B1 * | 4/2003 | Walker et al. | 705/26.35 |
| 6,571,213 B1 | 5/2003 | Altendahl et al. | |
| 6,622,084 B2 | 9/2003 | Cardno et al. | |
| 6,631,184 B1 | 10/2003 | Weiner | |
| 6,701,311 B2 | 3/2004 | Biebesheimer et al. | |
| 6,711,548 B1 | 3/2004 | Rosenblatt | |
| 6,715,073 B1 | 3/2004 | An et al. | |
| 6,816,882 B1 | 11/2004 | Conner et al. | |
| 6,839,679 B1 * | 1/2005 | Lynch et al. | 705/5 |
| 6,842,737 B1 | 1/2005 | Stiles et al. | |
| 6,847,988 B2 | 1/2005 | Toyouchi et al. | |
| 6,901,387 B2 | 5/2005 | Wells et al. | |
| 6,904,411 B2 | 6/2005 | Hinkle | |
| 6,920,431 B2 | 7/2005 | Showghi et al. | |
| 6,947,816 B2 | 9/2005 | Chen | |
| 6,959,298 B1 | 10/2005 | Silverbrook et al. | |
| 6,959,327 B1 | 10/2005 | Vogl et al. | |
| 6,961,773 B2 | 11/2005 | Hartman et al. | |
| 6,965,868 B1 | 11/2005 | Bednarek | |
| 6,970,831 B1 | 11/2005 | Anderson et al. | |
| 6,980,885 B2 | 12/2005 | Ye et al. | |
| 7,006,986 B1 | 2/2006 | Sines et al. | |
| 7,050,986 B1 | 5/2006 | Vance et al. | |
| 7,076,451 B1 * | 7/2006 | Coupland et al. | 705/5 |
| 7,080,096 B1 * | 7/2006 | Imamura | 707/104.1 |
| 7,117,170 B1 | 10/2006 | Bennett et al. | |
| 7,136,821 B1 * | 11/2006 | Kohavi et al. | 705/5 |
| 7,139,728 B2 | 11/2006 | Rigole | |
| 7,165,036 B2 | 1/2007 | Kruk et al. | |
| 7,194,417 B1 | 3/2007 | Jones | |
| 7,206,763 B2 | 4/2007 | Turk | |
| 7,206,768 B1 | 4/2007 | deGroeve et al. | |
| 7,222,084 B2 | 5/2007 | Archibald et al. | |
| 7,228,313 B1 | 6/2007 | Hand et al. | |
| 7,236,957 B2 | 6/2007 | Crosson | |
| 7,236,976 B2 | 6/2007 | Breitenbach et al. | |
| 7,272,568 B1 | 9/2007 | Birch et al. | |
| 7,272,626 B2 | 9/2007 | Sahai et al. | |
| 7,302,399 B1 | 11/2007 | Donovan et al. | |
| 7,315,824 B2 | 1/2008 | Chen et al. | |
| 7,343,312 B2 | 3/2008 | Capek et al. | |
| 7,343,338 B2 | 3/2008 | Etkin | |
| 7,356,516 B2 | 4/2008 | Richey et al. | |
| 7,363,242 B2 * | 4/2008 | Lewis et al. | 705/5 |
| 7,363,267 B1 | 4/2008 | Vincent et al. | |
| 7,379,890 B2 * | 5/2008 | Myr et al. | 705/7.35 |
| 7,379,900 B1 * | 5/2008 | Wren | 705/26.3 |
| 7,383,231 B2 | 6/2008 | Gupta et al. | |
| 7,388,495 B2 | 6/2008 | Fallin et al. | |
| 7,401,029 B2 | 7/2008 | Gillespie | |
| 7,415,419 B2 * | 8/2008 | Widjaja et al. | 705/5 |
| 7,451,106 B1 * | 11/2008 | Gindlesperger | 705/37 |
| 7,457,950 B1 | 11/2008 | Brickell et al. | |
| 7,472,080 B2 * | 12/2008 | Goel | 705/5 |
| 7,490,122 B2 | 2/2009 | Horvitz et al. | |
| 7,496,520 B1 | 2/2009 | Handel | |
| 7,499,864 B2 | 3/2009 | Campbell et al. | |
| 7,539,620 B2 * | 5/2009 | Winterton et al. | 705/1.1 |
| 7,548,615 B2 * | 6/2009 | Bhalgat et al. | 379/114.14 |
| 7,562,027 B1 | 7/2009 | Baggett et al. | |
| 7,574,372 B2 * | 8/2009 | Among et al. | 705/6 |
| 7,587,370 B2 * | 9/2009 | Himmelstein | 705/80 |
| 7,596,566 B1 | 9/2009 | Patwardhan | |
| 7,599,877 B1 | 10/2009 | Cole et al. | |
| 7,617,136 B1 * | 11/2009 | Lessing et al. | 705/28 |
| 7,660,743 B1 | 2/2010 | Messa et al. | |
| 7,743,002 B2 | 6/2010 | Hernandez | |
| 7,937,330 B2 | 5/2011 | Handel et al. | |
| 7,966,213 B2 | 6/2011 | Messa et al. | |
| 8,126,776 B2 | 2/2012 | Messa | |
| 2001/0003815 A1 | 6/2001 | Nakano | |
| 2001/0047289 A1 * | 11/2001 | Mckee et al. | 705/9 |
| 2001/0051917 A1 | 12/2001 | Bissonette et al. | |
| 2002/0010612 A1 | 1/2002 | Smith et al. | |
| 2002/0016729 A1 | 2/2002 | Breitenbach et al. | |
| 2002/0059092 A1 | 5/2002 | Naito et al. | |
| 2002/0065689 A1 | 5/2002 | Bingham et al. | |
| 2002/0069093 A1 * | 6/2002 | Stanfield | 705/5 |
| 2002/0095347 A1 | 7/2002 | Cummiskey | |
| 2002/0103693 A1 | 8/2002 | Bayer et al. | |
| 2002/0111872 A1 * | 8/2002 | Brice et al. | 705/26 |
| 2002/0111886 A1 | 8/2002 | Chenevich et al. | |
| 2002/0120478 A1 | 8/2002 | Tanaka | |
| 2002/0120548 A1 | 8/2002 | Etkin | |
| 2002/0143677 A1 | 10/2002 | Prakash | |
| 2002/0152101 A1 | 10/2002 | Lawson et al. | |
| 2002/0156684 A1 | 10/2002 | Stone et al. | |
| 2002/0156687 A1 | 10/2002 | Carr et al. | |
| 2002/0173978 A1 | 11/2002 | Boies et al. | |
| 2002/0184059 A1 | 12/2002 | Offutt et al. | |
| 2002/0184102 A1 * | 12/2002 | Markopoulos et al. | 705/26 |
| 2003/0023463 A1 | 1/2003 | Dombroski et al. | |
| 2003/0036930 A1 * | 2/2003 | Matos et al. | 705/5 |
| 2003/0036981 A1 | 2/2003 | Vaughan et al. | |
| 2003/0040987 A1 | 2/2003 | Hudson et al. | |
| 2003/0046195 A1 | 3/2003 | Mao | |
| 2003/0050879 A1 | 3/2003 | Rosen et al. | |
| 2003/0061145 A1 | 3/2003 | Norrid | |
| 2003/0078800 A1 | 4/2003 | Salle et al. | |
| 2003/0105711 A1 | 6/2003 | O'Neil | |
| 2003/0110062 A1 | 6/2003 | Mogler et al. | |
| 2003/0110136 A1 | 6/2003 | Wells et al. | |
| 2003/0120477 A1 | 6/2003 | Kruk et al. | |
| 2003/0120526 A1 | 6/2003 | Altman et al. | |
| 2003/0149653 A1 | 8/2003 | Penney et al. | |
| 2003/0177045 A1 | 9/2003 | Fitzgerald et al. | |
| 2003/0182413 A1 * | 9/2003 | Allen et al. | 709/223 |
| 2003/0191725 A1 * | 10/2003 | Ratliff et al. | 705/400 |
| 2003/0200111 A1 | 10/2003 | Damji | |
| 2003/0204474 A1 | 10/2003 | Capek et al. | |
| 2003/0229529 A1 | 12/2003 | Mui et al. | |
| 2003/0236722 A1 | 12/2003 | Kamel | |
| 2004/0002876 A1 | 1/2004 | Sommers et al. | |
| 2004/0034593 A1 | 2/2004 | Toneguzzo et al. | |
| 2004/0044556 A1 | 3/2004 | Brady et al. | |
| 2004/0044600 A1 | 3/2004 | Chu et al. | |
| 2004/0044644 A1 | 3/2004 | Brady et al. | |
| 2004/0044673 A1 | 3/2004 | Brady et al. | |
| 2004/0044681 A1 | 3/2004 | Brady et al. | |
| 2004/0049413 A1 | 3/2004 | Momma et al. | |
| 2004/0064351 A1 | 4/2004 | Mikurak | |
| 2004/0073615 A1 | 4/2004 | Darling | |
| 2004/0098606 A1 | 5/2004 | Tan et al. | |
| 2004/0117275 A1 | 6/2004 | Billera | |
| 2004/0143498 A1 | 7/2004 | Umeda | |
| 2004/0143522 A1 | 7/2004 | Wall et al. | |
| 2004/0148219 A1 | 7/2004 | Norris | |
| 2004/0153348 A1 | 8/2004 | Garback | |
| 2004/0167808 A1 | 8/2004 | Fredericks et al. | |
| 2004/0193457 A1 | 9/2004 | Shogren | |
| 2004/0210472 A1 | 10/2004 | Fujimoto et al. | |
| 2004/0249684 A1 | 12/2004 | Karppinen | |
| 2004/0249745 A1 | 12/2004 | Baaren | |
| 2004/0260601 A1 | 12/2004 | Brief | |
| 2004/0260603 A1 | 12/2004 | Marmotta | |
| 2005/0004819 A1 | 1/2005 | Etzioni et al. | |
| 2005/0004830 A1 | 1/2005 | Rozell et al. | |
| 2005/0033614 A1 | 2/2005 | Lettovsky et al. | |
| 2005/0033616 A1 * | 2/2005 | Vavul et al. | 705/5 |
| 2005/0033631 A1 | 2/2005 | Wefers et al. | |
| 2005/0043985 A1 | 2/2005 | Gillespie | |
| 2005/0043996 A1 | 2/2005 | Silver | |
| 2005/0060271 A1 | 3/2005 | Vig | |

(56) References Cited

U.S. PATENT DOCUMENTS

| | | | |
|---|---|---|---|
| 2005/0065821 A1* | 3/2005 | Kalies, Jr. | 705/2 |
| 2005/0086088 A1* | 4/2005 | Stiles et al. | 705/5 |
| 2005/0108069 A1 | 5/2005 | Shiran et al. | |
| 2005/0108153 A1 | 5/2005 | Thomas et al. | |
| 2005/0119809 A1* | 6/2005 | Chen | 701/33 |
| 2005/0119931 A1 | 6/2005 | Schall | |
| 2005/0120052 A1 | 6/2005 | Miller et al. | |
| 2005/0132006 A1 | 6/2005 | Horvitz et al. | |
| 2005/0138175 A1 | 6/2005 | Kumar et al. | |
| 2005/0165629 A1 | 7/2005 | Bruns | |
| 2005/0182713 A1 | 8/2005 | Marchesi | |
| 2005/0197913 A1 | 9/2005 | Grendel et al. | |
| 2005/0197915 A1 | 9/2005 | Biwer et al. | |
| 2005/0216375 A1 | 9/2005 | Grendel et al. | |
| 2005/0273345 A1 | 12/2005 | Castillejo | |
| 2005/0283389 A1* | 12/2005 | Widjaja et al. | 705/5 |
| 2005/0288973 A1 | 12/2005 | Taylor et al. | |
| 2006/0010023 A1 | 1/2006 | Tromczynski et al. | |
| 2006/0037016 A1 | 2/2006 | Saha et al. | |
| 2006/0059021 A1 | 3/2006 | Yulman et al. | |
| 2006/0100909 A1 | 5/2006 | Glimp et al. | |
| 2006/0101467 A1 | 5/2006 | Buco et al. | |
| 2006/0123088 A1 | 6/2006 | Simmons et al. | |
| 2006/0143087 A1 | 6/2006 | Tripp et al. | |
| 2006/0190314 A1 | 8/2006 | Hernandez | |
| 2006/0212321 A1 | 9/2006 | Vance et al. | |
| 2006/0224423 A1 | 10/2006 | Sun et al. | |
| 2006/0241966 A1 | 10/2006 | Walker et al. | |
| 2006/0259335 A1* | 11/2006 | La Macchia et al. | 705/6 |
| 2006/0277115 A1* | 12/2006 | McKee et al. | 705/26 |
| 2006/0283935 A1 | 12/2006 | Henry et al. | |
| 2006/0287897 A1* | 12/2006 | Sobalvarro et al. | 705/5 |
| 2007/0005406 A1 | 1/2007 | Assadian et al. | |
| 2007/0016439 A1* | 1/2007 | Stiles et al. | 705/1 |
| 2007/0021991 A1* | 1/2007 | Etzioni et al. | 705/5 |
| 2007/0038566 A1 | 2/2007 | Shestakov et al. | |
| 2007/0043651 A1* | 2/2007 | Xiao et al. | 705/37 |
| 2007/0118440 A1 | 5/2007 | Etkin | |
| 2007/0156546 A1 | 7/2007 | Oppert et al. | |
| 2007/0174154 A1* | 7/2007 | Roberts et al. | 705/30 |
| 2007/0239548 A1 | 10/2007 | Sears | |
| 2007/0273499 A1 | 11/2007 | Chlubek et al. | |
| 2008/0004964 A1 | 1/2008 | Messa | |
| 2008/0065408 A1 | 3/2008 | Salonen | |
| 2008/0091481 A1 | 4/2008 | Messa | |
| 2008/0319808 A1 | 12/2008 | Wofford et al. | |
| 2009/0006142 A1 | 1/2009 | Orttung | |
| 2009/0125355 A1 | 5/2009 | Handel | |
| 2009/0240566 A1 | 9/2009 | Lovegreen et al. | |
| 2010/0161432 A1 | 6/2010 | Kumanov et al. | |
| 2010/0191572 A1 | 7/2010 | Newman et al. | |
| 2011/0173092 A1 | 7/2011 | Werbitt | |

OTHER PUBLICATIONS

Handel, Sean et al., U.S. Appl. No. 11/187,484, entitled "System and Method for Optimization of Group Shipments to Reduce Shipping Costs," filed Jul. 22, 2005.
Messa, Suzette et al., U.S. Appl. No. 10/966,556, entitled "System for Optimization of Cost Management," filed Oct. 15, 2004.
Orttung, Mark et al., U.S. Appl. No. 11/027,115, entitled Apparatus and Method to Provide Community Pricing, filed Dec. 30, 2004.
Orttung, Mark et al., U.S. Appl. No. 11/178,033, entitled "Flexible Policy Application to Reduce Travel Costs," filed Jul. 7, 2005.
Patwardhan, Shantau et al., U.S. Appl. No. 11/066,022, entitled System and Method for Flexible Handling of Rules and Regulations in Temporary Labor Hiring, filed Feb. 24, 2005.
Satterlee Stephens Burke & Burke, LLP, "Tax Consequences of Frequent Flyer Mileage Earned on Business Travel," located at http://www.ssbb.com/freqfly.html, May 1997.
Transaction History of U.S. Appl. No. 10/966,556, filed Oct. 15, 2004, entitled "System for Optimization of Cost Management."
Transaction History of U.S. Appl. No. 11/027,115, filed Dec. 30, 2004, entitled "Apparatus and Method to Provide Community Pricing."
Transaction History of U.S. Appl. No. 11/066,022, filed Feb. 24, 2005, entitled "System and Method for Flexible Handling of Rules and Regulations in Temporary Labor Hiring."
Transaction History of U.S. Appl. No. 11/178,033, filed Jul. 7, 2005, entitled "Flexible Policy Application to Reduce Travel Costs."
Transaction History of U.S. Appl. No. 11/187,484, filed Jul. 22, 2005, entitled "System and Method for Optimization of Group Shipments to Reduce Shipping Costs."
Transaction History of U.S. Appl. No. 11/240,740, filed Sep. 30, 2005, entitled "Method and System for Testing of Policies to Determine Cost Savings."
Transaction History of U.S. Appl. No. 11/319,911, filed Dec. 27, 2005, entitled "Method and System for Ranking Services on a Variable Scale of Compliance."
Transaction History of U.S. Appl. No. 11/324,083, filed Dec. 29, 2005, entitled "Method and System to Provide Cumulative Budget and Probabilities for a Return on Expenditure for Policy Enforcement."
Transaction History of U.S. Appl. No. 11/480,106, filed Jun. 30, 2007, entitled "Method and Systems for Personal Restaurant Assistant."
Transaction History of U.S. Appl. No. 11/549,957, filed Oct. 16, 2006, entitled "System and Method for Automatic Review of Travel Changes and Improved Suggestions and Rules Set."
Transaction History of U.S. Appl. No. 11/768,882, filed Jun. 26, 2007, entitled "System and Method for Tracking Spending Based on Reservations and Payments."
Aberdeen Group, Inc., "Xerox Scraps Paper for an Automated Expense Management Solution and Sees Multiple Millions in Return," Aberdeen Group OnSite: Best Practices, 2002.
Amadeus IT Group SA, "End to End Travel Management from Travel Booking to Expense Management," May 2, 2007.
Business Editors, "Accenture and Captura Form Alliance to Provide Web-Enabled Expense Management Solutions," Business Wire, Aug. 13, 2001.
Datasheet, Gelco Reservation Manager 2.0, Gelco Information Network, Inc., 2003.
Extensity, Inc., "Extensity, Amadeus and e-Travel Team to Provide Integrated Travel and Expense Management Solution," Oct. 24, 2001.
Fair Isaac Corporation, "What's in Your Score," www.myfico.com, Feb. 9, 2005.
Farber, Dan, "Rearden Commerce Transforms Business Services," ZDNet, Feb. 27, 2005.
IBM Corporation, "American Express, IBM Join Forces to Offer Easy-to-Use Online Tool for Reporting, Reconciling Business Expenses," Mar. 5, 2002.
IBM Corporation, "IBM Introduces Electronic Expense Reporting Solution to Help Companies Eliminate Reimbursement Paper Trail" Aug. 3, 1998.
Zhu, Guangyu et al., "Extracting Relevant Named Entities for Automated Expense Reimbursement," Proceedings of the 13th ACM SIGKDD International Conference on Knowledge Discovery and Data Mining, San Jose, CA, Aug. 2007.
Elliff, Scott, "Who's Who?: Sorting out the E-Logistics Players," Logistics Management & Distribution Report, pp. E3-E9, Apr. 2001.
Mullen, Theo, "Services Compare Shipping Costs Instantly," InternetWeek, p. 9, Jun. 12, 2000.
PR Newswire Association, Inc., "WorldTravel BTI Enhances Non-Refundable Tracker with Comprehensive Tracking and Reporting: Improved Offering Helps Corporations Understand and Manage Their Non-Refundable Ticket Patterns," PR Newswire, Jun. 4, 2003.

* cited by examiner

📄 Airlines, Sun Nov 21. Microsoft Internet Explorer

Tools   Help

📁🏠 🔎 Search ⭐ Favorites 🎞 Media 🕘 ✉ ▾ 📂 [W]   ⟵ 500

Settings\northung\Mark's Data\Products\OldDocs\Travelprototypes\Email Demov3\Small Grapemailv1.htm
⟵ 501

TALARIS
Group Member Itinerary Booked For
Forrester Research Meeting
November 24, 2002
9AM - 2PM (EST)
24 Forrester Place
Waltham, MA  02123            502

Patrick Grady Has booked his itinerary for the Forrester Research Meeting. Please use the buttons at the end of the email to book a similar itinerary.

San Francisco (SFO) to Boston (BOS)
   Flights: American Airlines #194
Departure: Sunday, November 23 at 2:05 PM
 Arrival: Sunday, November 23 at 10:31 PM
 Seating: Economy Class, 20F Boston (BOS) to San Francisco (SFO)
   Flights: American Airlines #197
Departure: Monday, November 24 at 8:10 PM
 Arrival: Sunday, November 24 at 8:37 PM
 Seating: Economy Class, 10C       503

Hotel: LE MERIDIEN BOSTON
   250 Franklin St, Boston, MA 02110
   1 517 451 1900 View Map
Check-in: Sunday, November 23
Check-out: Monday, November 24

Car: Hertz
   On Airport (BOS)
 Class: Compact
 Pick-up: Sunday, November 23
511⟶  Drop-off: Monday, November 24 ⟵512     ⟵513

Book Identical Itinerary  Book Air and Hotel, Share Car  Meet at Airport, Share car
Meet at Hotel ⟵514                                                510

Thank for using Talaris. Have a great meeting.

FIG. 5

COST MODEL ANALYSIS AND BREAKDOWN FOR COST BUILDUP

RELATED APPLICATIONS

This application is related to U.S. application Ser. No. 10/943,608, entitled "Delegation of Travel Arrangements by a Temporary Agent," filed Sep. 17, 2004, which is incorporated herein by reference.

FIELD OF THE INVENTION

This invention relates generally to procurement of services, and more particularly to coordinating the group procurement of services.

BACKGROUND OF THE INVENTION

In the usual course of doing business, service providers, particularly travel service providers, frequently add numerous and varied fees and surcharges to the basic cost of a service. In some cases the total of the extra fees may approach or even surpass the cost of the base services. Therefore, it is important for customers of such service provider to track those fees. Moreover, fees among different providers are not always comparable, and many service providers purposely do not list or otherwise bring to light those fees, because hiding the fees and surcharges allows them to protect some high margin revenues.

What is clearly needed is a system and method for breaking out and estimating the various fees and surcharges charged by each service provider to an organization or to individuals in general that uses the services of competing providers, rather than listing just a basic negotiated service fee, thus allowing a true comparison of the overall cost of the purchased services.

To optimize the cost of purchased services to travel provisioning systems, such as travel arrangers and/or organizations, collected information about the cost structures of such service providers, for example, hotels, airlines, and others, may be used to make a comparative analysis. To make such an analysis, a breakdown of the costs into their components is necessary. Currently, no models for such an approach are known to the inventors to exist in the market. What is used is a market-price-based approach, but the problem with that approach is that if two companies are inefficient in different areas, their market price may be the same, so any opportunity to achieve savings is not visible.

What is clearly needed is a system and method to refine and support an analysis of the costs and cost breakdowns for services provided to a services provisioning system by allowing users to compare costs of components of services provided, extracting and comparing information of actual billing, and allowing users to mix and match the lowest-cost services or allowing users to direct cost savings into preferred partners.

SUMMARY OF THE INVENTION

One embodiment of the invention includes a method and system to obtain data for fees and surcharges charged by multiple providers for multiple services based on prior interactions with the service providers, and provide an estimate for fees and surcharges to be charged by one of the service providers for one of the services based on the prior interactions with the service providers. In one embodiment, the fee data is extracted from one of electronic publishing of fees, billings for services rendered, and employee expense reports. In one embodiment, the estimated fees and surcharges include restricted access to a first subset of data to a first predetermined group.

The present invention describes systems, clients, servers, methods, and computer-readable media of varying scope. In addition to the aspects and advantages of the present invention described in this summary, further aspects and advantages of the invention will become apparent by reference to the drawings and by reading the detailed description that follows.

BRIEF DESCRIPTION OF THE DRAWINGS

FIG. 5 illustrates a screen shot as it would be seen by a group member, in accordance with one embodiment;

DETAILED DESCRIPTION OF THE INVENTION

In the following detailed description of embodiments of the invention, reference is made to the accompanying drawings in which like references indicate similar elements, and in which is shown by way of illustration specific embodiments in which the invention may be practiced. These embodiments are described in sufficient detail to enable those skilled in the art to practice the invention, and it is to be understood that other embodiments may be utilized and that logical, mechanical, electrical, functional, and other changes may be made without departing from the scope of the present invention. The following detailed description is, therefore, not to be taken in a limiting sense, and the scope of the present invention is defined only by the appended claims.

Automatic Service Exchange

Figure 1A:
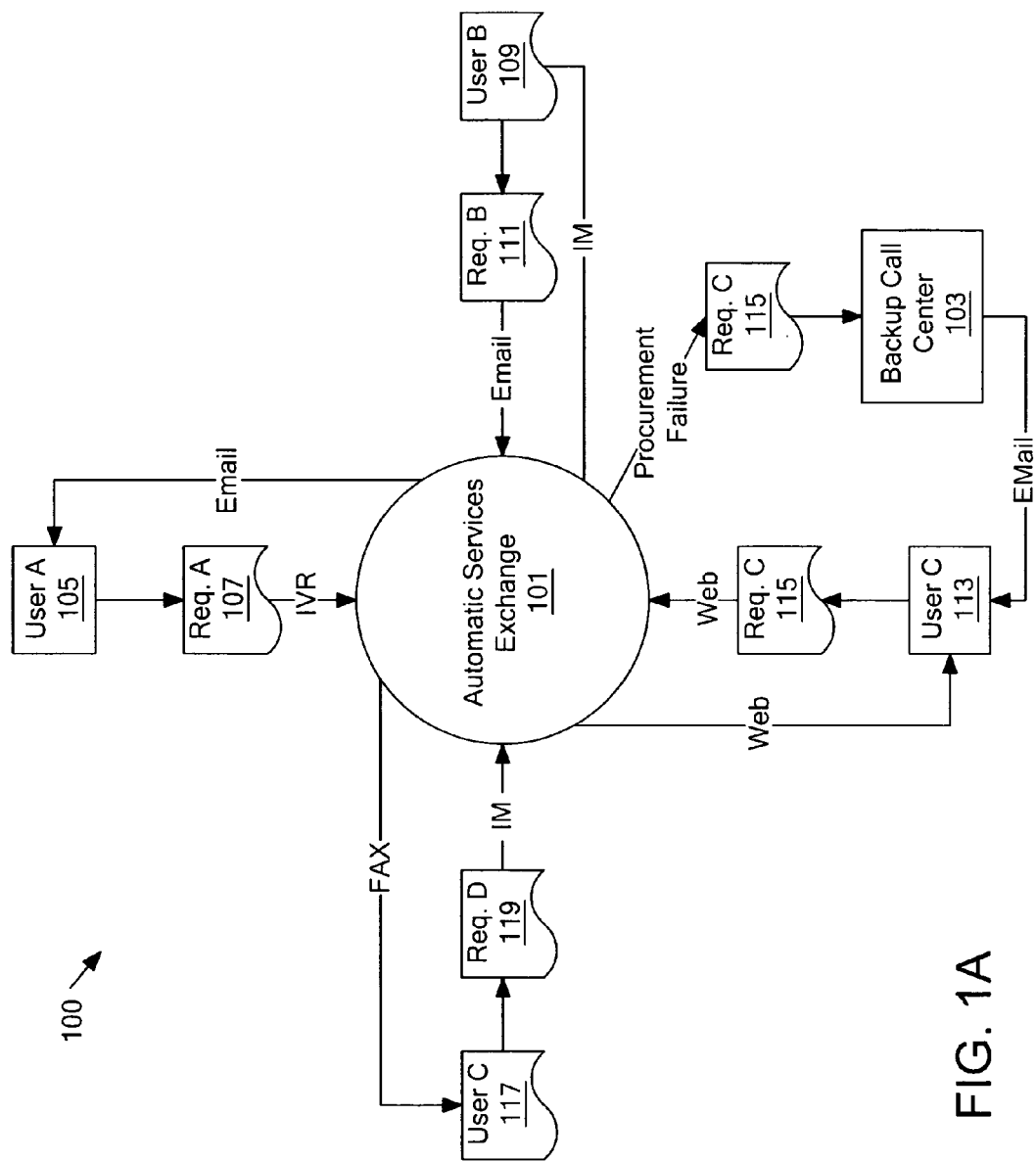
FIGS. 1A-C are diagrams illustrating a system-level overview of an embodiment of the invention.

A system level overview of the operation of one embodiment of an automatic services exchange system 100 is described by reference to FIGS. 1A-C. In FIG. 1A, the automatic services exchange system 100 is illustrated as having an automatic services exchange component 101 and an optional call center backup component 103. The automatic services exchange component 101 allows users such as a user A 105, user B 109, user C 113, and user D 117 to request services from the exchange. The service requests may be sent to the exchange component 101 through various communication media. For example, user A 105 sends its request A 107 to the exchange component 101 through an interactive voice response system (IVR), user B 109 sends its request B 111 to the exchange component 101 through e-mail (typically a structured e-mail), user C 113 sends its request C 115 via a Web browser, such as Internet Explorer or Netscape or a micro-browser on a WAP enabled cellular telephone, and user D 117 send its request D 119 through an instant messaging system (IM). These different communication media typically have different data formats, such as structured e-mail, or an Internet based markup language such as XML, or IVR voice recognition. Regardless of the communication media used to send the request to the exchange component 101, a response to a request may be sent back to the user through a different media. Thus, FIG. 1A illustrates that user A 105 receives its response through e-mail, user B 109 receives its response via instant messaging, and user D 117 receives its response via fax. In the case of user C 113, the same communication medium, Web, used to send the request is also used to send the response.

The services available through the exchange component 101 include travel services, entertainment service, personal services (e.g., haircutting), educational services, business administrative services and the like. Some services may be time critical, e.g., a dinner reservation at a particular time. The service request specifies other required criteria for the service, such as location (e.g., a certain geographic area), type, duration, quantity, price information (e.g., preferred price or price range and maximum price), etc. Additionally, a single service request may actually require services from multiple different service providers which are linked or associated. For example, if a user is planning a business trip, the request will often require services from airlines, hotels and car rental agencies and perhaps other services which are linked to or associated with the business trip.

The automatic services exchange component 101 automatically sends the service request to various service providers. In one embodiment, this transmission may be through several different electronic communication media such as structured e-mail, XML, IVR, etc. In the event that the exchange component 101 is unable to automatically procure the service requested by the user, the request is transferred to the backup call center component 103. For example, assume that request C 115 from user C 113 could not be automatically fulfilled by the exchange component 101. As illustrated in FIG. 1A, the request C 115 is sent to the backup call center 103 along with other information such as which service providers have already been contacted for the service. One of the human agents or operators at the backup call center 103 attempts to find a service provider for the request. Once the backup call center 103 determines that the request can or cannot be satisfied, it communicates the result to the corresponding user who made the request. In the example, the result is sent to user C 113 through e-mail.

Figure 1B:
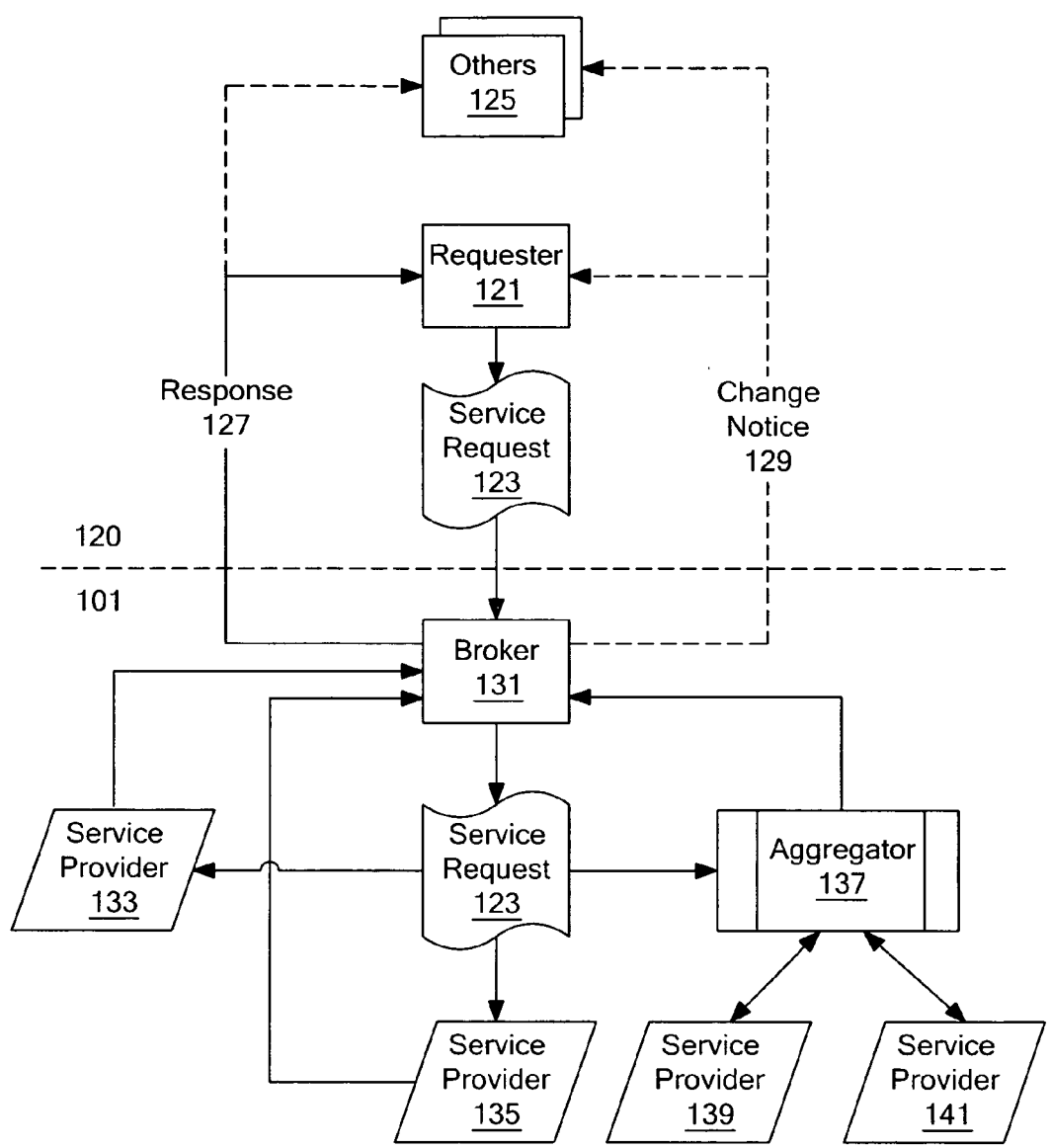
Figure 1C:
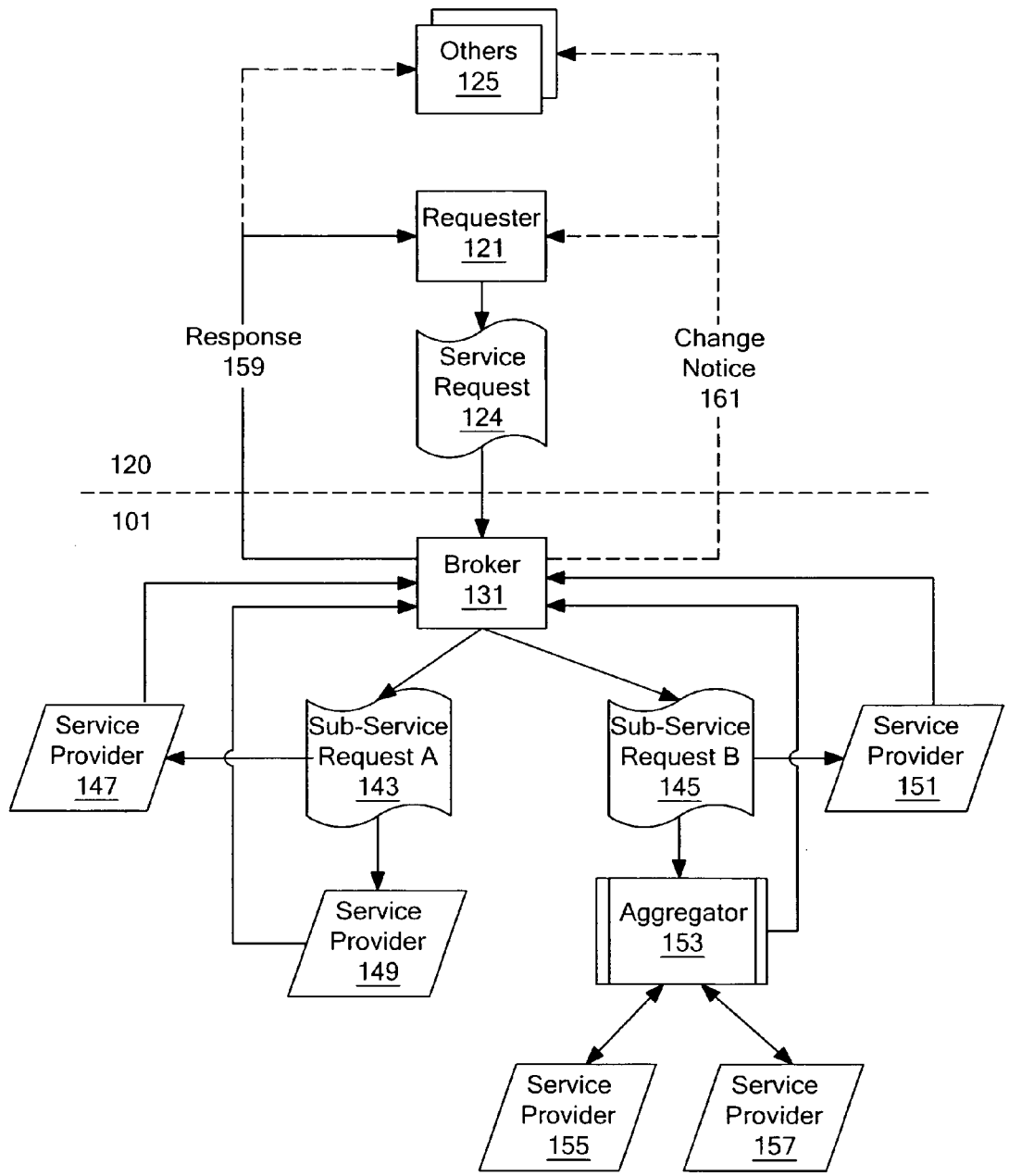

FIGS. 1B and 1C show the operation of the automatic services exchange component 101 in more detail. In FIG. 1B, a requestor 121 sends a service request 123 to the automatic services exchange 101. A broker function 131 receives a service request and passes it onto various service providers, such as service provider 133 and service provider 135. The service request may also be sent to an aggregator that represents multiple service providers, such as aggregator 137 that handles requests for service provider 139 and service provider 141, instead of directly to the service providers. In one embodiment, the service request is sent using an automatic system, such as an IVR system, that asks for a positive or negative reply to the request (e.g., a voice over the telephone says "press 1 if you have a table for two at 6:30 p.m. at your restaurant on XYZ date, press 2 if you do not"). Each of the service providers 133, 135 and the aggregator 137 replies to the broker 131 indicating whether they are able to provide the requested service. The responses to broker 131 may be through different communication media such as the Internet (e.g., via an XML page), structured e-mail, or IVR.

Assuming there is at least one positive reply, the broker 131 sends a response 127 to the requestor 121 with the results indicating at least one response matched the request. Depending on parameters set by the requestor 121, if multiple positive replies are received by the broker 131, the broker may choose the best match based on the required or predetermined criteria or it may send responses for all the positive replies to the requestor 121 for selection. The requestor 121 may also authorize the broker 131 to contract for the service under certain circumstances without waiting for approval from the requestor 121. A match to request typically means that the response from the service provider is within the range of acceptable requesting parameters such as time of service, location of service, price of service, level (e.g., quality requested) of service, and other parameters specified by the request.

As illustrated in phantom in FIG. 1B, the broker 131 may also send the response 127 to others 125 specified by the requestor 121. For example, when multiple people are planning a dinner, one person, the requester 121, may be in charge of obtaining the reservation, but the other people involved should receive notification of the particulars.

Also shown in phantom in FIG. 1B, is the capability of sending a change notice 129 to the requestor 121 if a procured service changes before its performance date. This change may occur by a modified request which is issued by the requestor 121. Similarly, the change notice 129 may also be sent to others 125 specified by the requestor 121. The requester can approve the change if the change is satisfactory, or submit a new service request if the change is unsatisfactory, or if the service is now unavailable from the original provider (not shown). The exchange system of the invention, in one embodiment, can automatically respond to a modified request.

The broker 131 reviews, through an automatic machine implemented process, the service requests to determine if the service request is actually a request for multiple services, such as multiple services which are linked or associated such as those associated with an event (e.g., a business trip which requires airline tickets, rental car reservation and hotel reservation). The resulting operation is illustrated in FIG. 1C. The broker 131 breaks such a request into sub-service requests 143 and 145 and sends each to the appropriate service providers. Thus, in FIG. 1C, sub-service request A 143 is sent to service providers 147, 149, while sub-service request B 145 is sent to service provider 151 and aggregator 153, which aggregates the services from service providers 155 and 157. As before, each service provider/aggregator typically returns a message to the broker 131 specifying its ability to provide the service. Each sub-service response 159 may be sent separately to the requestor 121 or the broker 131 may wait until all service providers/aggregators have responded or until a match to each sub-service request has been found. As in FIG. 1C, change notices 161 also will be sent to the user 121 upon a change in a procured service. Additionally, the responses 159 and the change notices 161 may be sent to others 125 specified by the requestor 121.

The particular methods of the invention are now described in terms of computer software with reference to a series of flowcharts. The methods to be performed by a computer constitute computer programs made up of computer-executable instructions illustrated as blocks (acts). Describing the methods by reference to a flowchart enables one skilled in the art to develop such programs including such instructions to carry out the methods on suitably configured computers (e.g., the processor of the computer executing the instructions from computer-readable media). The computer-executable instructions may be written in a computer programming language or may be embodied in firmware logic. If written in a programming language conforming to a recognized standard, such instructions can be executed on a variety of hardware platforms and for interface to a variety of operating systems. In addition, the present invention is not described with reference to any particular programming language. It will be appreciated that a variety of programming languages may be used to implement the teachings of the invention as described herein. Furthermore, it is common in the art to speak of software, in one form or another (e.g., program, procedure, process, application, module, logic . . . ), as taking an action or causing a result. Such expressions are merely a shorthand way of saying that execution of the software by a computer causes the processor of the computer to perform an action or a produce a result.

Figure 2A:
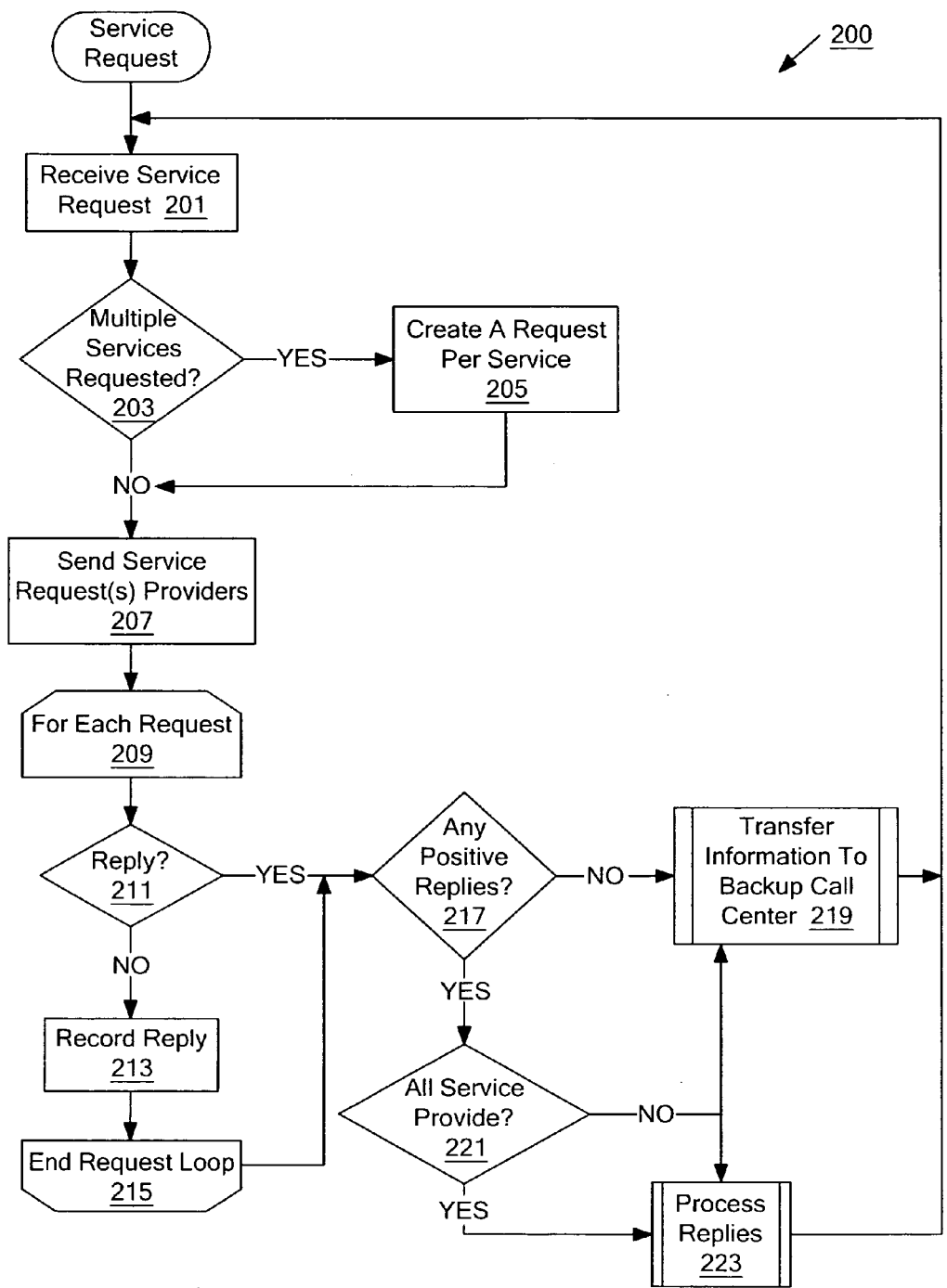
FIGS. 2A-C are flowcharts of methods to be performed typically by computers in executing the embodiment of the invention illustrated in FIGS. 1A-C.
Figure 2B:
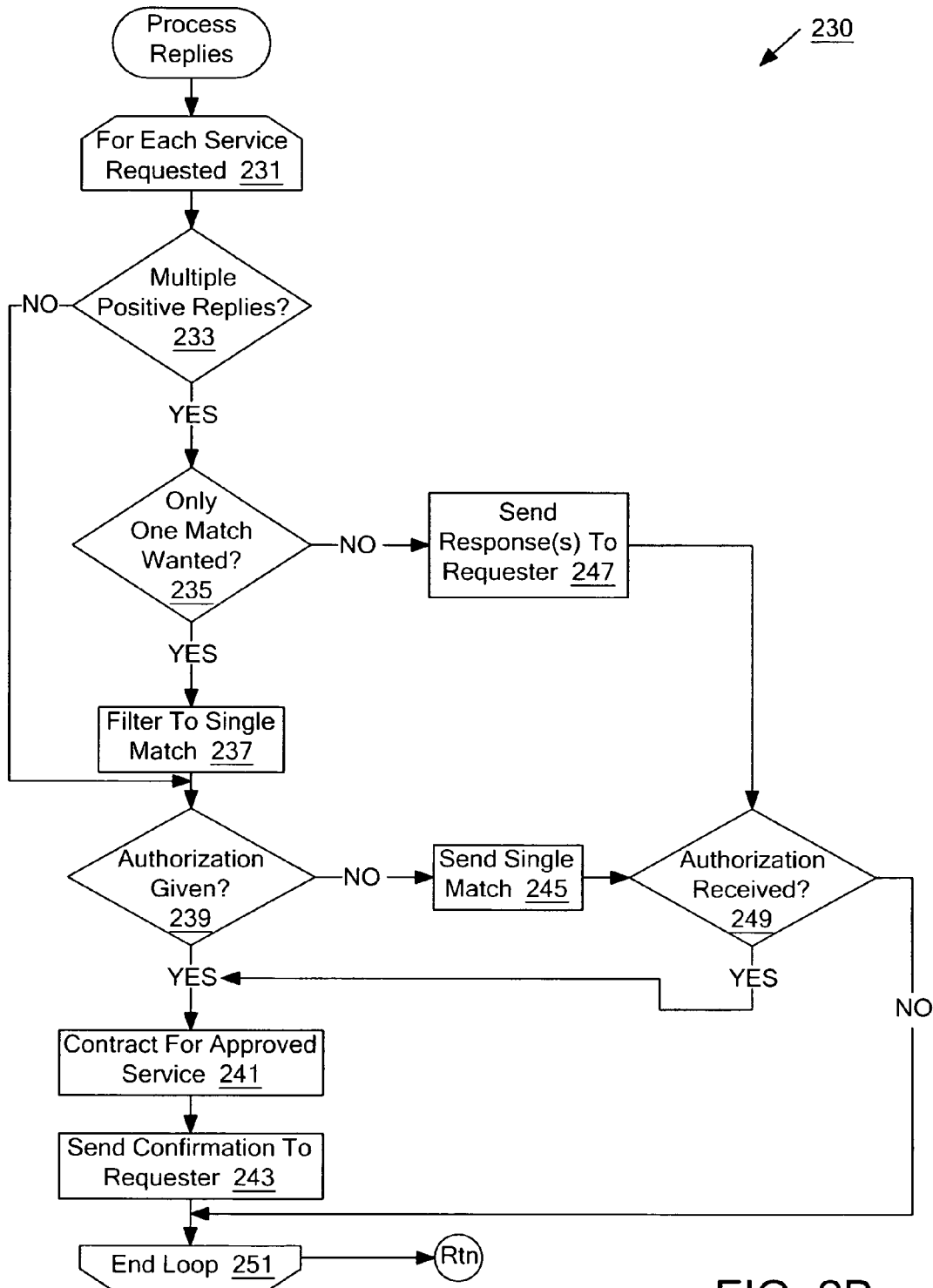
Figure 2C:
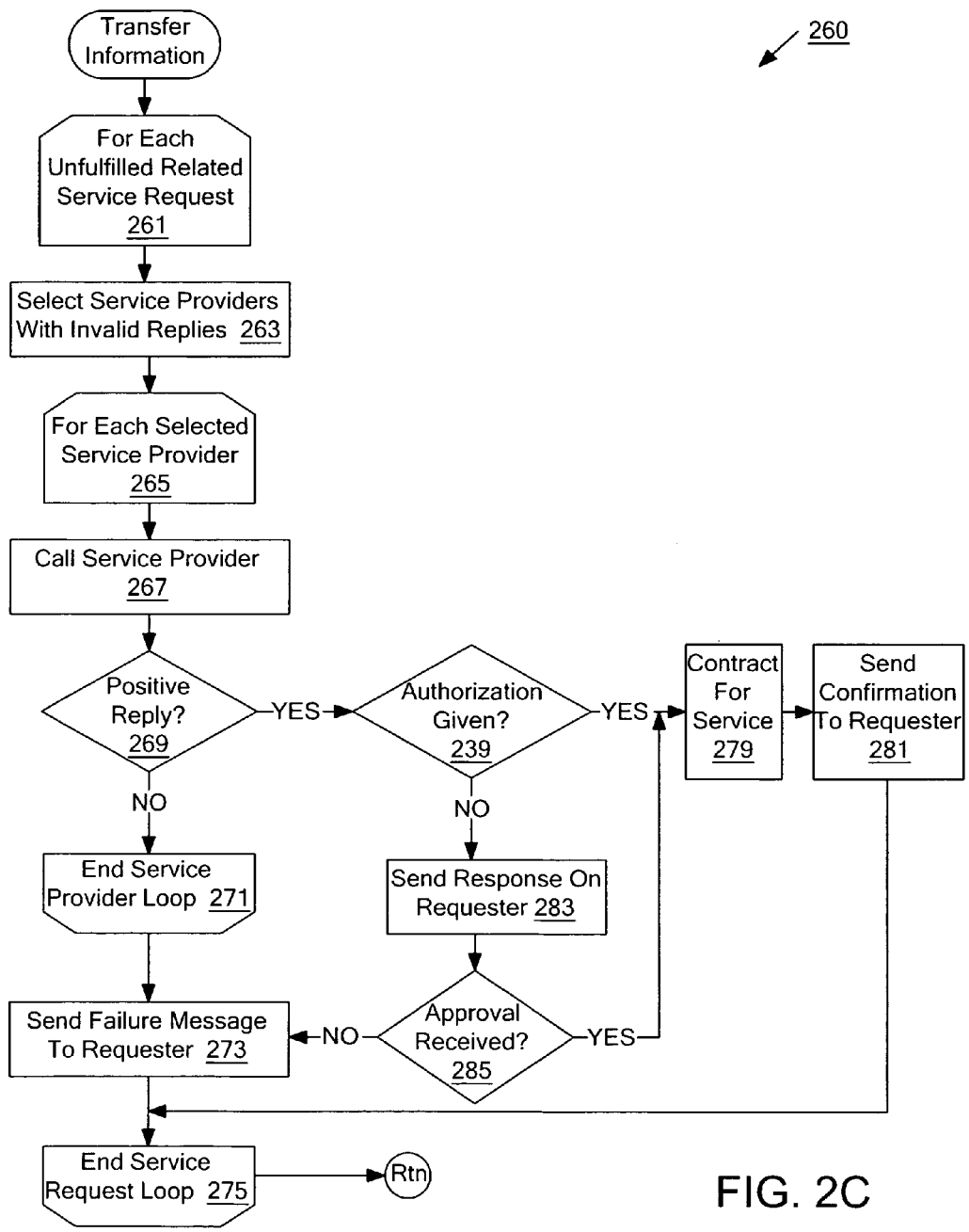
Figure 3:
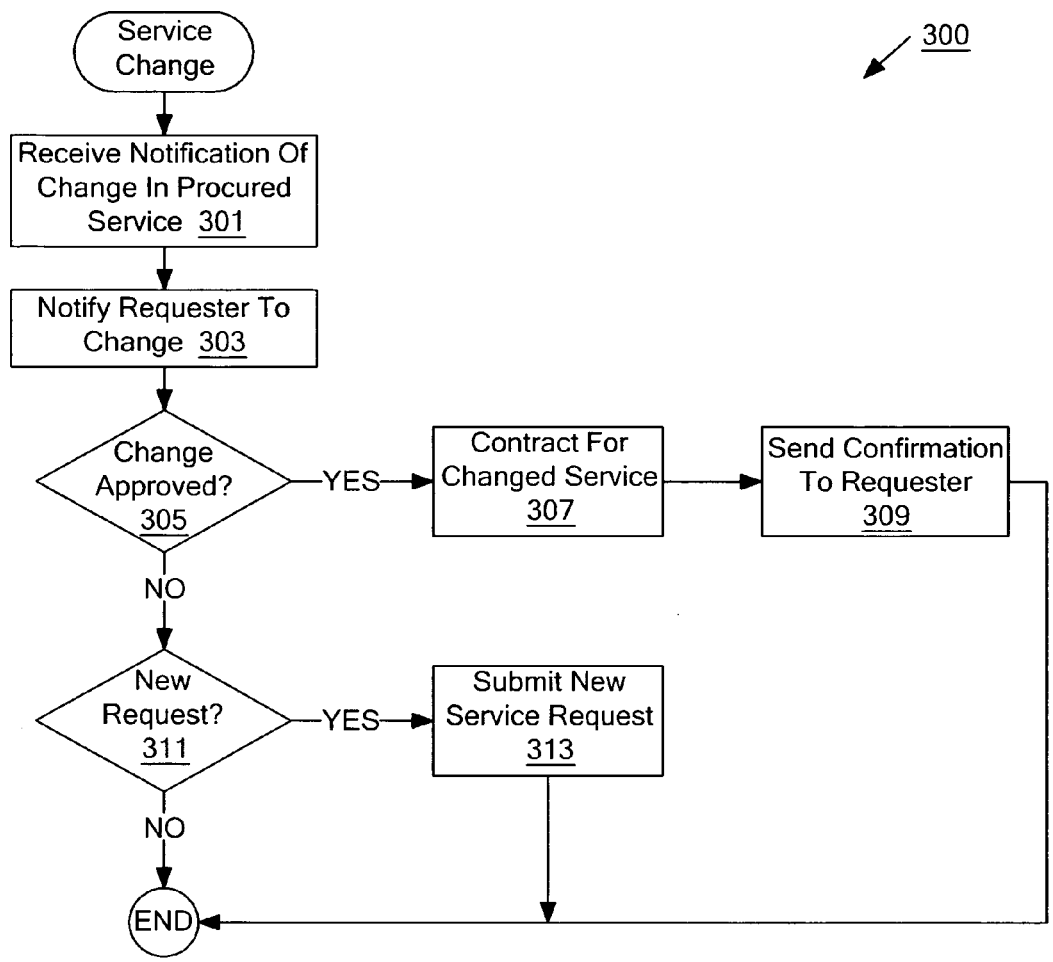
FIG. 3 is a flowchart of an optional method to be performed by a computer in executing the embodiment of the invention illustrated in FIGS. 1A-C.

FIGS. 2A and 2B illustrate the acts to be performed by a computer, or set of computers, acting as the automatic services exchange component 101 of FIG. 1A in processing service requests. FIG. 2C illustrates the acts to be performed by a computer acting in conjunction with the backup call center 103 in FIG. 1A. FIG. 3 illustrates the acts to be performed by the computer acting as the automatic services exchange component when the optional change notification is desired.

Referring first to FIG. 2A, a service request method 200 receives a service request method (block 201) and examines it to determine if there are multiple, related services requested (block 203). If so, the service request method 200 creates a request for each service (block 205). Once the multiple requests are created, or if there is only one request, the service requests are sent to the appropriate providers (including aggregators) for the services (block 207).

The service request method 200 processes the replies for each request separately as illustrated by request loop starting at block 209. It will be appreciated that multiple request loops may be running concurrently. The requestor may specify a time which is associated with a deadline for completion of a search for a match to a request. In one embodiment, the requestor specifies a predetermined required period of time (time out period or deadline) within which replies must be received or by which time the requestor should be contacted by the exchange to inform the requestor of the incomplete status of a request. In another embodiment, the time out period is determined by the method 200 based on time criteria specified in the request. The request loop waits at block 209 until an incoming reply is received or until the time out period expires. When the request loop is activated by an incoming reply (block 211), the reply is recorded at block 213. If all replies have not yet been received, the request loop returns to its wait state. If all replies have been received, the particular request loop ends (block 215) and the method 200 proceeds to block 217 to evaluate the replies. Alternatively, if the time out period expires before any or all replies are received, the method 200 also proceeds to block 217. The time out period can provide the exchange system with some time to attempt to "manually" (through the intervention of a human operator) procure the service with enough time before the service is actually required. If the user/requestor fails to specify a time out period, the exchange system may specify a default time out period which is at least several hours before the requested time of the service (e.g., a 4:30 p.m. time out for a dinner reservation at 7:30 p.m.) or at least one day before the requested date of the service. Further, this time out period also allows the requestor to be notified of a failure to procure a service before the time requested for the service so that the requestor can take appropriate actions.

At block 217, the method 200 determines if any positive replies were received. If not, the corresponding request is transferred to the backup call center (which includes human operators) for processing along with all replies (block 219) so the backup call center knows the current status of the request (e.g., who has replied to the request, who has not, etc.). The processing represented by block 219 is described in more detail in conjunction with FIG. 2C further below.

If multiple services were requested, the method 200 determines if at least one service provider has replied positively to each service request (block 221). Requests that cannot been procured are sent to the backup call center at block 219, while positive replies are processed at block 223 (e.g., by sending out confirmations to the requestor and the service providers to secure the providing of the service). Similarly, if only one service was requested and at least one reply is positive, the method 200 proceeds to block 223 to process the reply. The processing represented by block 223 is described next.

One embodiment of a process reply method 230 is illustrated in FIG. 2B. It will be appreciated that multiple instances of the method 230 may be executing simultaneously based on the number of service requests that were made. For each service requested (block 231), the process reply method 230 determines if multiple positive replies for a service were received (block 233). If so, but only one match has been requested (block 235), the method 230 filters the replies to find a single match that best satisfies the criteria specified by the requestor (or specified as defaults by the system of the exchange service) (block 237). If there was only one positive reply for the service, or once a single reply has been filtered out in block 237, the method 230 determines if the requestor has authorized the automatic services exchange system to automatically procure the service (block 239). If so, the method 230 contracts or otherwise reserves the service from the corresponding service provider (block 241) and sends a confirmation request confirmation to the requestor that the service has been procured (block 243). In these situations where the service provider requires a commitment (e.g., a down payment or a deposit) from the requestor, the automatic services exchange provides payment information (e.g., credit card name, number and expiration date) previously provided by the requestor to the automatic services exchange or requests that this information be provided by the requestor to either the exchange (so it can be forwarded to the service provider) or to the service provider directly. If, however, there is no authorization (block 239), the information in the reply is sent to the requestor at block 245 and the method 230 waits to receive approval from the requestor. If approval is received (block 249), the method 230 contracts for or otherwise reserves the approved service and sends a confirmation as previously described. However, if approval of the particular service is not received from the requestor, the service request is terminated.

If more than one match is wanted at block 235 (as specified by a predetermined preference sent by the requestor or as set as a default by a system of the exchange service), a response containing all positive replies is sent to the requestor for selection (block 247) and the method 230 waits to receive approval of one of the providers at block 249. As in the case of a single reply, the method 230 contracts for or otherwise reserves the service from the approved provider at block 241 and returns a confirmation message at block 243, or the request is terminated if no approval is received.

Turning now to FIG. 2C, one embodiment of an information transfer method 260 for a backup call center is illustrated. When the service request is sent to the providers through an automatic system, a reply may be invalid such as when a person, in response to questions from an IVR system, presses an incorrect digit on a telephone key pad or hangs up without replying or if the call is unanswered. For each unfulfilled related service request (block 261), the method 260 selects those service providers that gave invalid replies (block 263). Each of the selected service providers (block 265) will be called by a human agent (block 267) until one provider is able to provide the service (block 269) or until all have been called (block 271). If no service provider can fulfill the service request, the method 260 sends a failure message to the requester at block 273. If there are no further related service requests (block 251), the method 260 terminates.

The first positive reply at block 269 causes the method 260 to determine if the requester has authorized the automatic services exchange system to automatically procure the service (block 277). If so, the method 260 contracts or otherwise reserves the service from the corresponding service provider (block 279) and sends a confirmation request confirmation to the requestor that the service has been procured (block 281). If, however, there is no authorization at block 277, the information in the reply is sent to the requestor (block 283) and the method 260 waits to receive approval from the requestor. If approval is received (block 285), the method 260 contracts for or otherwise reserves the approved service and sends a confirmation as previously described. However, if approval of the particular service is not received from the requestor, a failure message is sent to the requester at block 272.

As described previously, the automatic services exchange system optionally can send change notices to the requester to alert him/her of changes in a procured service or receive a modified request from the requestor even after the services have been procured. One embodiment of a service change method 300 that communicates changes is illustrated in FIG. 3. When the method 300 receives notification of a change in a procured service (block 301), it notifies the requester and asks if the requester approves the change or wishes to submit a new service request (block 303). If the change is approved (block 305), a message is sent to the service provider to contract for the changed service (block 307) and the change is confirmed to the requester (block 309). If the change is not approved but a new service request is submitted (block 311), the new request is resubmitted into the automatic services exchange system at block 313.

The particular methods performed by computers acting as the automatic services exchange and backup call center components for one embodiment of the invention have been described with reference to flowcharts in FIGS. 2A-C and 3, including all the acts from 201 until 223, from 231 until 251, from 261 until 285, and 301 until 313, respectively. It will be appreciated that more or fewer processes may be incorporated into the methods illustrated in FIGS. 2A-C and 3 without departing from the scope of the invention and that no particular order is implied by the arrangement of blocks shown and described herein and that alternative orders of the operations are within the scope of the invention.

Figure 4A:
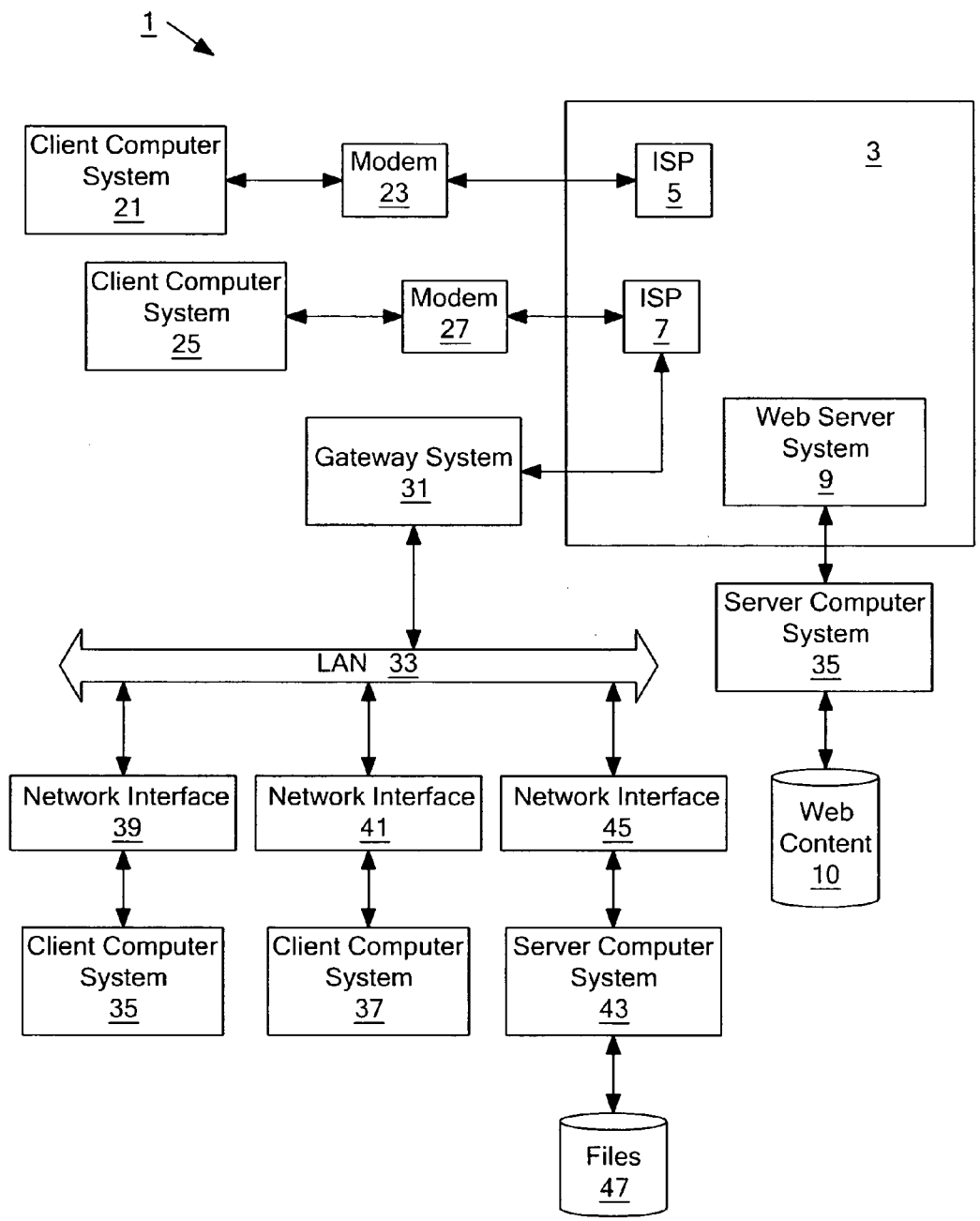
FIG. 4A is a diagram of one embodiment of an operating environment suitable for practicing the present invention.
Figure 4B:
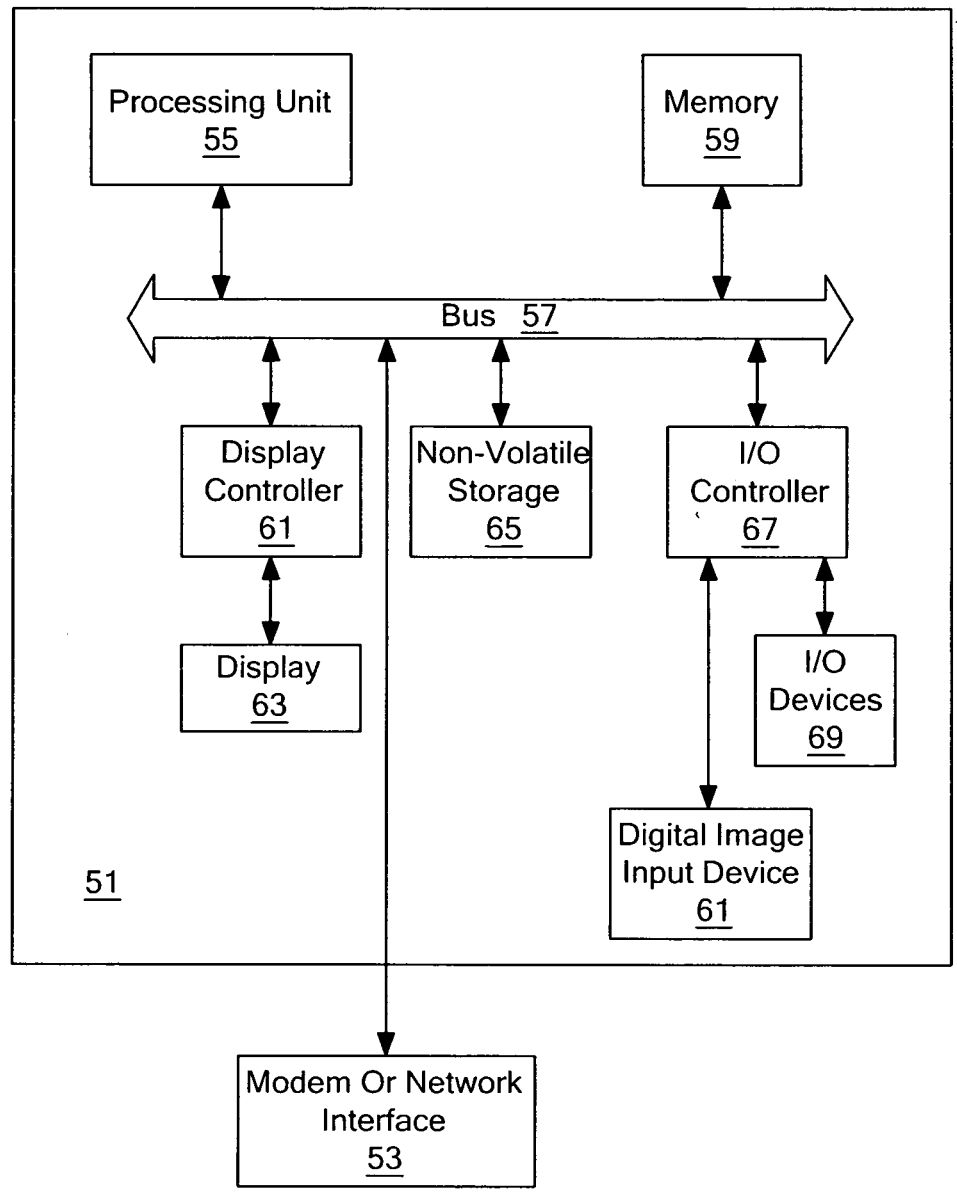
FIG. 4B is a diagram of one embodiment of a computer system suitable for use in the operating environment of FIG. 4A.

The following description of FIGS. 4A-B is intended to provide an overview of computer hardware and other operating components suitable for performing the methods of the invention described above, but is not intended to limit the applicable environments. One of skill in the art will immediately appreciate that the invention can be practiced with other computer system configurations, including hand-held devices (e.g., PDAs—personal digital assistants such as a Palm Pilot; or cell phones, etc.), multiprocessor systems, microprocessor-based or programmable consumer electronics, network PCs, minicomputers, mainframe computers, and the like. The invention can also be practiced in distributed computing environments where tasks are performed by remote processing devices that are linked through a communications network having a physical or wireless infrastructure, or a combination of both.

FIG. 4A shows several computer systems that are coupled together through a network 3, such as the Internet. The term "Internet" as used herein refers to a network of networks which uses certain protocols, such as the TCP/IP protocol, and possibly other protocols such as the hypertext transfer protocol (HTTP) for hypertext markup language (HTML) documents that make up the World Wide Web (web). The physical connections of the Internet and the protocols and communication procedures of the Internet are well known to those of skill in the art. Access to the Internet 3 is typically provided by Internet service providers (ISP), such as the ISPs 5 and 7, through either physical or wireless interfaces. Users on client systems, such as client computer systems 21, 25, 35, and 37 obtain access to the Internet through the Internet service providers, such as ISPs 5 and 7. Access to the Internet allows users of the client computer systems to exchange information, receive and send e-mails, and view documents, such as documents which have been prepared in the HTML format. These documents are often provided by web servers, such as web server 9 which is considered to be "on" the Internet. Often these web servers are provided by the ISPs, such as ISP 5, although a computer system can be set up and connected to the Internet without that system being also an ISP as is well known in the art.

The web server 9 is typically at least one computer system which operates as a server computer system and is configured to operate with the protocols of the World Wide Web and is coupled to the Internet. Optionally, the web server 9 can be part of an ISP which provides access to the Internet for client systems. The web server 9 is shown coupled to the server computer system 11 which itself is coupled to web content 10, which can be considered a form of a media database. It will be appreciated that while two computer systems 9 and 11 are shown in FIG. 4A, the web server system 9 and the server computer system 11 can be one computer system having different software components providing the web server functionality and the server functionality provided by the server computer system 11 which will be described further below.

Client computer systems 21, 25, 35, and 37 can each, with the appropriate web browsing software, view HTML pages provided by the web server 9. The ISP 5 provides Internet connectivity to the client computer system 21 through the modem interface 23 which can be considered part of the client computer system 21. The client computer system can be a personal computer system, a network computer, a Web TV system, a handheld wireless device, or other such computer system. Similarly, the ISP 7 provides Internet connectivity for client systems 25, 35, and 37, although as shown in FIG. 4A, the connections are not the same for these three computer systems. Client computer system 25 is coupled through a modem interface 27 while client computer systems 35 and 37 are part of a LAN. While FIG. 4A shows the interfaces 23 and 27 as generically as a "modem," it will be appreciated that each of these interfaces can be an analog modem, ISDN modem, cable modem, satellite transmission interface (e.g., "Direct PC"), radio frequency (RF), cellular, or other interfaces for coupling a computer system to other computer systems. Client computer systems 35 and 37 are coupled to a LAN 33 through network interfaces 39 and 41, which can be Ethernet network or other network interfaces. The LAN 33 is also coupled to a gateway computer system 31 which can provide firewall and other Internet related services for the local area network. This gateway computer system 31 is coupled to the ISP 7 to provide Internet connectivity to the client computer systems 35 and 37. The gateway computer system 31 can be a conventional server computer system. Also, the web server system 9 can be a conventional server computer system.

Alternatively, as well-known, a server computer system 43 can be directly coupled to the LAN 33 through a network interface 45 to provide files 47 and other services to the clients 35, 37, without the need to connect to the Internet through the gateway system 31.

FIG. 4B shows one example of a conventional computer system that can be used as a client computer system or a server computer system or as a web server system. It will also be appreciated that such a computer system can be used to perform many of the functions of an Internet service provider, such as ISP 5. The computer system 51 interfaces to external systems through the modem or network interface 53. It will be appreciated that the modem or network interface 53 can be considered to be part of the computer system 51. This interface 53 can be an analog modem, ISDN modem, cable modem, token ring interface, satellite transmission interface (e.g., "Direct PC"), radio frequency (RF), cellular, or other interfaces for coupling a computer system to other computer systems. The computer system 51 includes a processing unit 55, which can be a conventional microprocessor such as an Intel Pentium microprocessor or Motorola Power PC microprocessor. Memory 59 is coupled to the processor 55 by a bus 57. Memory 59 can be dynamic random access memory (DRAM) and can also include static RAM (SRAM). The bus 57 couples the processor 55 to the memory 59 and also to non-volatile storage 65 and to display controller 61 and to the input/output (I/O) controller 67. The display controller 61 controls in the conventional manner a display on a display device 63 which can be a cathode ray tube (CRT) or liquid crystal display. The input/output devices 69 can include a keyboard, disk drives, printers, a scanner, and other input and output devices, including a mouse or other pointing device. The display controller 61 and the I/O controller 67 can be implemented with conventional well known technology. A digital image input device 61 can be a digital camera which is coupled to an I/O controller 67 in order to allow images from the digital camera to be input into the computer system 51. The non-volatile storage 65 is often a magnetic hard disk, an optical disk, or another form of storage for large amounts of data. Some of this data is often written, by a direct memory access process, into memory 59 during execution of software in the computer system 51. One of skill in the art will immediately recognize that the term "computer-readable medium" includes any type of storage device that is accessible by the processor 55 and also encompasses a carrier wave that encodes a data signal.

It will be appreciated that the computer system 51 is one example of many possible computer systems which have different architectures. For example, personal computers based on an Intel microprocessor often have multiple buses, one of which can be an input/output (I/O) bus for the peripherals and one that directly connects the processor 55 and the memory 59 (often referred to as a memory bus). The buses are connected together through bridge components that perform any necessary translation due to differing bus protocols.

Network computers are another type of computer system that can be used with the present invention.

Network computers do not usually include a hard disk or other mass storage, and the executable programs are loaded from a network connection into the memory 59 for execution by the processor 55. A Web TV system, which is known in the art, is also considered to be a computer system according to the present invention, but it may lack some of the features shown in FIG. 4B, such as certain input or output devices. A typical computer system will usually include at least a processor, memory, and a bus coupling the memory to the processor. Further, mobile devices, such as PDAs, browsing web phones etc. and their respective supporting infrastructure may also be used as clients etc.

It will also be appreciated that the computer system 51 is controlled by operating system software which includes a file management system, such as a disk operating system, which is part of the operating system software. One example of an operating system software with its associated file management system software is the family of operating systems known as Windows® from Microsoft Corporation of Redmond, Wash., and their associated file management systems. The file management system is typically stored in the non-volatile storage 65 and causes the processor 55 to execute the various acts required by the operating system to input and output data and to store data in memory, including storing files on the non-volatile storage 65.

Coordination for Group Procurement of Services

One embodiment of the present invention permits group members to add additional reservations onto an existing reservation of a group leader, supervisor or any other member of the group in such a manner as to synchronize travel plans and coordinate locations, etc., both in terms of travel time, sharing rides, staying at the same hotel, tee times, and other services one may desire when attending an event. But rather than book all group members at once, individual group members may make plans separately, to accommodate instances in which group members are, for example, traveling from different locations, or are arriving at different times, etc. For example, a sales person may be coming from a different customer site in another city, while the marketing person and the technical person may be coming from the home office.

FIG. 5 shows a screen as it would be seen by such a group member. The data as displayed on the screen may be shared with the group members via an Internet media, or other alternative media. Section 500 is the header bar of the browser window, and section 501 is the application window for a specific set of services—in this case, travel and accommodations for a business meeting at a customer site. Heading section 502 for the event shows that members of the company Talaris are visiting Forrester Research in Waltham, Mass. Group members can see the travel itinerary of the group leader respectively the first person to book travel in section 503. As each member books travel and other services related to the meeting, the system automatically notifies, via the Internet or other media, the other members of the group and asks if they want to book identical travel services or similar travel services (e.g., start in a different location and ultimately end up at a destination together at a specific time). The system automatically would also coordinate sharing of resources such as a rental car or hotel rooms. Further, the system would enforce corporate policies related to the services being procured. For example, the system might require employees to share a rental car, a limo, a shuttle bus etc. if two or more employees are traveling on a similar trip.

Thus in the example embodiment shown in FIG. 5, group members have the options shown in section 510 to choose one of four travel options. It is clear that in other example embodiments, other, similar options, additional options, or fewer options may be offered. Section 511 is an option to book an identical itinerary, which would be suitable for a person starting the trip from the same location at the same time. This option allows group members to travel together. Section 512 allows group members to book separate, identical air and hotel reservations, but has them share a single car rental; section 513 allows members to meet at the airport upon arrival (in this example, at the Boston airport) so a group member flying in from, for example, New York, could meet with members flying in from San Francisco, to share the car into Walton; and section 514 allows for only booking rooms at the same hotel, so group members may come and go separately but stay at the same hotel, allowing them to meet and travel together to the company site conveniently.

The system illustrated in FIG. 5 is just one embodiment of the novel art of this disclosure for automated coordination of services procurement for a group of individuals involved in a common goal or event. In this and other embodiments, one of the individuals (the leader) would define the attributes of the event and specify the other individuals to be involved in the event (the "group"). All of the individuals would be automatically notified, via the Internet or other media, by the system that they are invited to participate in the goal or event, and all individuals would be able to accept or decline membership in the group event or goal, in some cases in accordance with company policies for such participation, expense rules, privacy rules etc. Likewise, all individuals who accept group membership would be able to procure a combination of services required to execute the event. All individuals who accepted the invitation to join the group would be notified of the booking of services by the other members of the group, and each individual in the group would be able to make a services procurement request for the services procured by any other individual or individual(s) in the group. The system is able to coordinate sharing of the services based on its understanding of the mutual requirements of the group, and is also able to adjust the services procured by members of the group to better meet the overall group's objectives. The system is likewise able to adjust the services procured by the members to optimize the use of the services by the group as a whole, or to intelligently cancel services based on changes in requirements input by one or more members of the group. In some cases, corporate policy may allow some participants to exceed their usual settings in context of a group event. In other cases, it may notify additionally their supervisor, procurement group, or human resources, and in yet other cases, it may require a confirmation by e-mail from a supervisor or similar. The type of services that may be procured are not limited to services related to travel, but rather may also include other services related to attending an event, or other activities to participate in while visiting a location.

Yet in some cases, if a member needs to come in late, for example due to a previous meeting, he may not share in some aspects, such as the share car ride for example etc. In other circumstances, if a member needs special facilities, not available at the hotel/car/flight chosen for the group, the member may break out of the group arrangements. This may be on a case by case basis, with approval and or notification of the group leader, his supervisor etc., or may be pre-defined in the member's profile in some cases.

Figure 6:
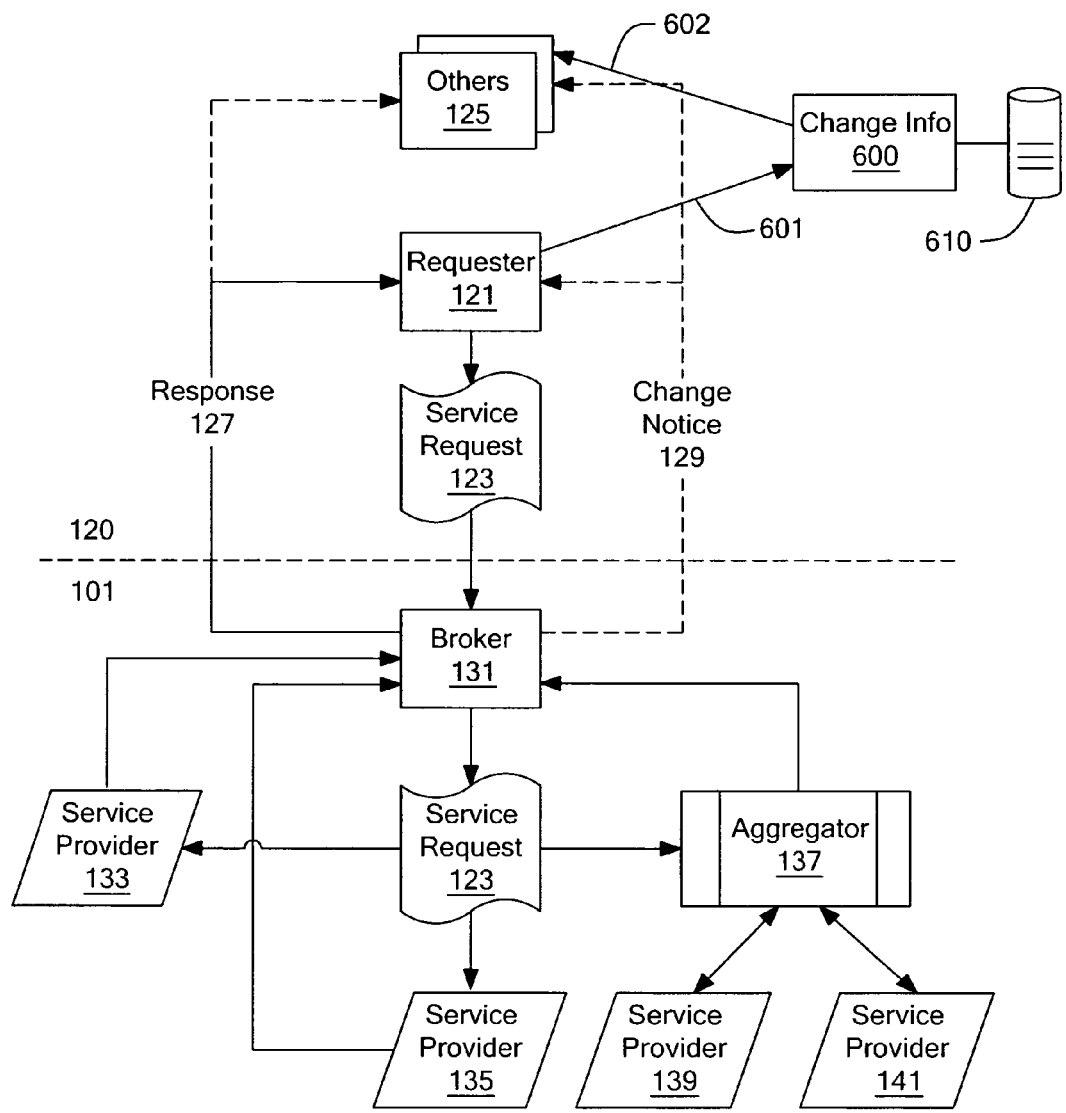
FIG. 6 illustrates block diagram of an alternative embodiment.

FIG. 6 illustrates a block diagram of an integration of the embodiment for providing coordination of group procurement of services integrated in the system of FIG. 1b, as discussed above. The integration includes the addition of a group information block 600 that allows the original requester 121 to export his travel plans via function 601 into block 600. The requester can assign group members into a group data base 610, so that when the designated group members log in as other users 125, they can see what travel options are available, pull them down via function 602, and then participate in making travel plans, as described above in relation to FIG. 5. Furthermore, as mentioned above, group member may receive a particular invitation, and in some cases, that may require a supervisor's approval.

In yet other cases, a user may be able to forward their service request in an automatic fashion. For example, a user could initiate a group by inviting others to join for a meeting at a specific date, time, and location. Once they have done this, they have formed a group. Once one member of the group has booked their travel for this particular meeting, they would be prompted to see if they are willing to share their itinerary with the other members of the group. If they give permission for the other members to see the itinerary, all other members of the group would be automatically notified by the system. When notified, the other members of the group would be given options to book similar or identical services. When other group members select an option, a service request such as (123) in FIG. 6 is automatically generated and sent to the services exchange.

Just before, or during, the travel unexpected events may occur that necessitate changes to the travel plans. For example, two parties may plan to travel and meet in a third city, but then one is delayed. To accommodate such occurrences, one embodiment of the present invention provides a process to automatically and dynamically identify an entity to adjust the pre-established travel plans to accommodate one or more of the travelers.

This rebooking of the flights and rides, etc., obviously could be done manually on a person-by-person basis, but preferably one group manager (e.g., an assistant or group member) could do the rebooking for the whole group. In one embodiment, the group manager doing the rebooking could be a robotic software agent or entity, being present as part of the reservation system and following certain preprogrammed rules.

Figure 7:
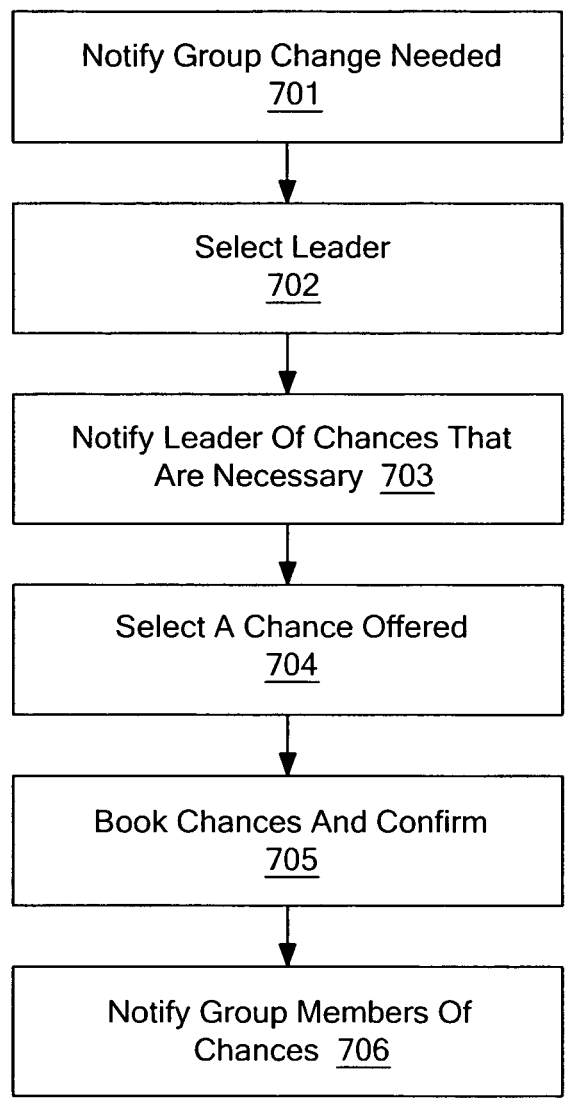
FIG. 7 illustrates a flow diagram describing the processes in accordance with one embodiment.

FIG. 7 presents a flow diagram of semi-automated service software instance 700 of the novel art of the current invention. This software instance 700 may execute for example on server 42 (FIG. 4A) and interact with all the modules necessary, acting as a Group Services Management System (GSMS). This software instance 700 is the entity to handle changes in travel arrangements according to the novel art of this disclosure. In step 701, the group whose event must be rebooked is identified to the system. This may be done separately by software (not shown), monitoring all services and events for which the group database 610 has bookings. When a change occurs, the GSMS 700 identifies in step 702, the group manager, previously selected when the group parameters were entered into the system. Said group manager could be a person, as noted earlier, or could be a robotic software agent (not shown). There also may be rules within the GSMS that if no human manager is identified, the manager may default to a robotic agent. Additionally, there may be rules to check a series of alternates, if the group manager is unavailable, until an available alternate is found.

In step 703, the GSMS notifies the manager of the changes that must take place to arrange rebooking all arrangements (different services, including such as hotel rooms, restaurant reservations, flights, limos, rental cars, deliveries etc.) of the event (locations, rides, hotel rooms, meetings, Web conferences, Audio conferences, catering, etc.). In some cases, the GSMS may need to offer alternatives. For example, a subset of invitees or listed attendees for a scheduled meeting (M1) that needs to be rescheduled, may be unable to attend the rescheduled meeting M1R (possibly due to a calendar conflict), and thus the meeting would have to be canceled.

Based on such scenarios, and rules as they may be stored for the event group in group database 610, or general rules of the enterprise or organization, in step 704 one or multiple options may be offered to the group manager, who may then make the decision and confirm selection of one among the offered options. In step 705, the GSMS rebooks arrangements as necessary and confirms all the arrangements, including flights, transportation, hotels, restaurants, etc. In step 706 the GSMS issues alerts and notifies all the parties in the group of the travel arrangements.

In one embodiment, it may be further useful for the system 700 according to the present invention also to know how to modify these options based on a user's profile. For example, a traveler's home location, unique starting destination, past list of flights, and/or necessary arrival times based for scheduled meetings of the traveler's original itinerary.

In one embodiment, the system might also do a quick calendar check before displaying the user's flight or other travel options, and show a visual alert to the respective traveler that existing travel arrangements may be in conflict with proposed changes.

Also, as changes occur in real time, a quick response is necessary, and in some cases, if an appointed group agent cannot respond in time, the system may escalate according to a set of rules to switch over to an automatic assumption of the role of group manager by the above-mentioned software agent. Such a change may be required, for example, if the group agent is on a plane himself, or in a different time zone, etc., and cannot be reached until after a time at which a decision for rebooking must be made. Alternatively, the system may escalate directly (i.e., if it knows the agent is not reachable) or it may first escalate to a backup designated agent. Further, in some cases, the system can automatically offer options to the user via email when they accept or decline original meeting invitation.

Furthermore, in some cases, the system can also take into account "criticality" of each resource and event when suggesting options or making decisions for the group. For instance, if the VP of Sales is designated as a critical person for a meeting, then first try to move his travel plans if meeting has to change. In case his requirements can't accommodate a new meeting time or location, then, for example, the system might not automatically move others, because meeting shouldn't happen without him.

It is clear, that many modifications may be made, without departing from the spirit of the invention. For example, a shared screen may be offered allowing all members of the group to concurrently view availability, and decide over a multitude of alternative options.

The embodiments as described herein allow for very efficient procurement of services, such as, for example, synchronization of business travel plans, within an existing organizational infrastructure. It also reduces the overhead for auxiliary personnel, such as assistants and secretaries trying to coordinate the plans of many group members. It is clear that many modifications and variations of this embodiment may be made by one skilled in the art without departing from the spirit of the novel art of this disclosure. For example, in some cases, such system and method can be used by consumers to similarly coordinate family gatherings/trips, etc.

Intelligent Meeting Planner

Figure 8:
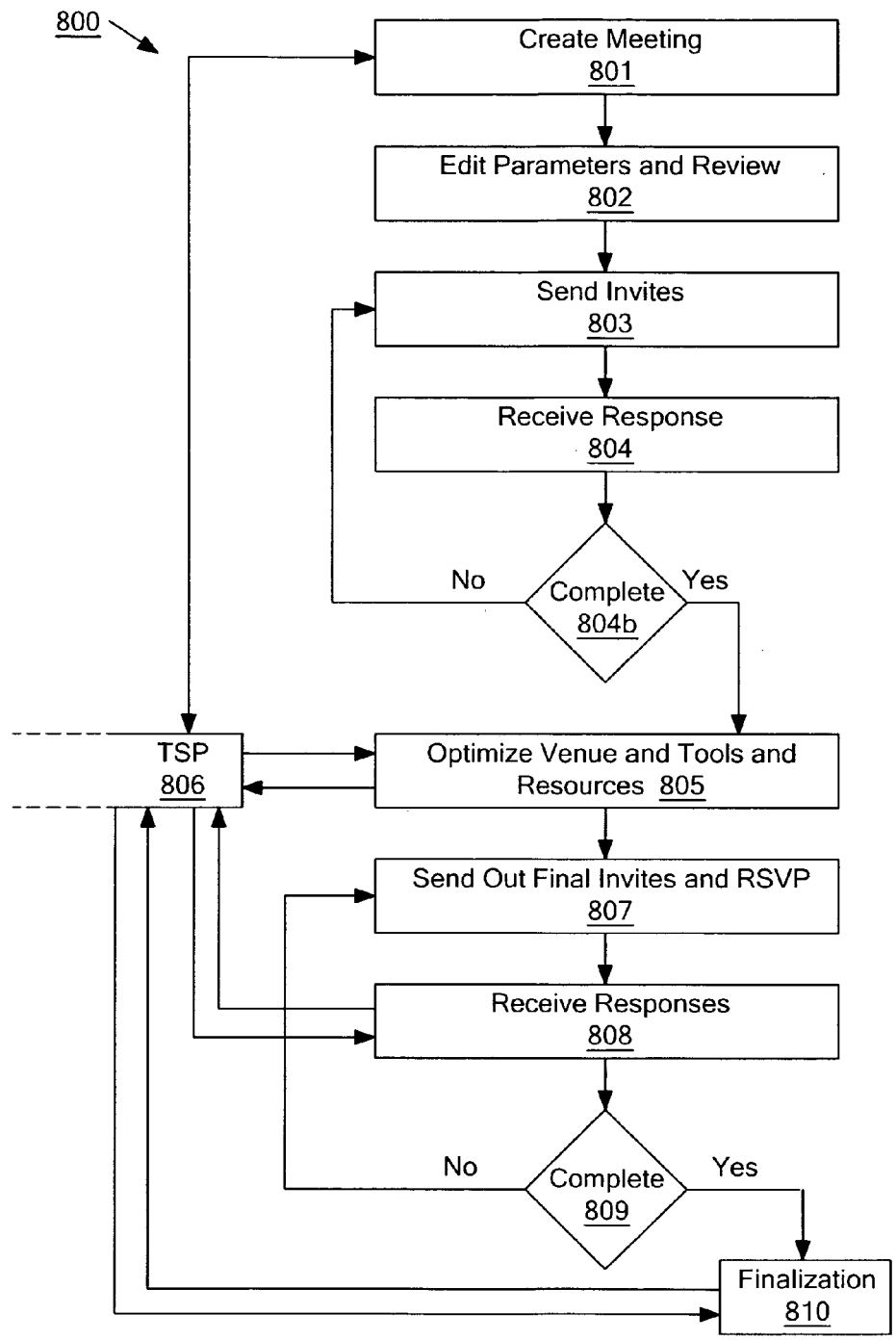
FIG. 8 illustrates a flow diagram describing the process in accordance with one embodiment.

FIG. 8 shows a simplified flow diagram of a meeting planner 800 according to the novel art of this disclosure. In step 801, a meeting is created in the meeting planner 800. In step 802, its parameters are edited and reviewed. Meeting parameters could be entered manually by the meeting organizer, or they could be taken from a template as a default beginning, or they could be selected from any of various templates describing meetings that are held on a regular basis, such as quarterly sales meeting, annual review meeting, monthly management meeting, etc. In some cases, meeting parameters could also be dictated by the responses received from the invitees. Fore example, if attendees say they are attending virtually, the meeting requirements would now include a web and audio bridge. It is clear, that many variants can be made that are not explicitly shown here, or below, without departing from the spirit of the invention.

The nature and purpose of the meeting dictates the list of people that must attend. In particular, some people may be required to attend in person, whereas others may be allowed, but not required, to attend in person. The system should allow the input of each person and a relative level of importance for attendance. In addition, the system should allow the input of whether each person is needed in person or if they can attend virtually. This will drive the dependencies of the service types and details scheduled by the system for the users. Yet others may not even be allowed to attend in person, but only to attend virtually. Based on the list of people and their attendance modes, already a certain number of venues may be considered, while others are eliminated. Additionally, because people are located in different places, arrangements must be made for their travel, accommodations, etc.

For example, if five people are to be in a meeting, two could be ranked as highly required to be present physically, meaning that the meeting cannot happen without their physical presence in the meeting location, two could be ranked as required, but can attend virtually; and one could be ranked as optional. The system would then look at their calendars and the service availability needed to pull this meeting together. For instance, if the predetermined meeting location is in New York and the Highly Required meeting attendee 1 is planning to be in San Francisco for a meeting at 8 pm-9 pm the previous day, the system would check for flights that leave at some time after the 9 pm meeting (likely starting at 11 pm to account for driving time to the airport and check-in time). If a flight leaves after 11 pm and arrives in time for the 9 am meeting in New York, including estimated driving time, then the system could auto-accept the meeting for that user and pre-plan all of his travel arrangements as well. If there is a conflict such that his physical presence cannot be accommodated at 9 am based on his previous meeting, the system would give the users the option of moving the 9 am meeting to 12 pm or some time that works for all involved parties. Once that time is vetted and accepted by the system rules and dependencies, then the meeting is scheduled and all ancillary services are automatically scheduled by the system, including travel arrangements, conference room reservations, web conference reservation, catering (for the number of people physically present), etc. If something about the meeting details or the attendees changes, the system would reexamine all of the dependencies and the services that are scheduled and make the appropriate adjustments to the meeting time, services or people attending.

Another feature of this system is the ability to find the best meeting time for a group of people. The meeting organizer can input into the system some of the details of the meeting such as desired location (if known), duration, agenda, invitees and their criticality to the meeting, including whether virtual or physical presence is required, etc. The system would then scan the invited attendees schedules (in Outlook, Notes, this system or some other system), determine who is required and who is not, determine if they can be present or not based on flight schedules and other dependencies, and either determine the optimal time and place to have the meeting or show the user a list of ranked options that he can choose from. Alternatively, the system can offer a bunch of predefined time and location options to the attendees and they can each respond with their preferences for each option. The system would then determine the optimal time based on these user-input preferences.

Based on the initial requirements of the meeting input in step 801, and the edit and review of parameters in step 802, invitations to the meeting are issued in step 803. Then responses to the invitations are received in step 804. In step 804*b*, the completeness of the those responses is compared to a pre-set threshold of completeness. The completeness does not have to be 100 percent, but if perhaps 80 percent have responded, that is enough to proceed with plans, or if 18 out of 25 persons who must attend in person have responded positively. This threshold used to decide completeness typically would also be part of the parameters set in step 802 above, but might be entered separately, or might conform to a set of corporate rules etc. (not shown). If the completeness level has not been achieved by a certain date, the process loops back to step 803 to send invitation reminders, and so on until the desired completeness level has been achieved.

The process then continues in step 805. Based on the responses and choices of the attendees, some of whom will attend in person and others of whom will attend virtually, a cost analysis is performed in step 805. This analysis optimizes both the venue and any travel costs involved, such as transportation (usually air), hotel, and any other required resources, such as auto rental, meals, and, for virtual attendees, the cost of using video-, web-, or teleconferencing equipment. This optimization happens in interaction with a services transaction system, such as the Talaris Services Platform 806, that is important to the novel art of this disclosure. This interaction optimizes the costs of all the meeting elements, taking into consideration less obvious cost aspects, such as time lost in travel and the salary value to the company of various attendees, so travel time is optimized not necessarily just by the number of people traveling, but by the total value to the company. Other parameters may be used as well to optimize value. Further, there may be certain limitations, such as that some people may be unable to travel, which would give them a greater weight in a decision made by the system, as compared to other people, just based on salary, lost work time, impacted projects, etc.

After all these optimizations have been done in step 805, in step 807 the system issues a final invitation with all the specifics of the meeting and venue, including an RSVP. The responses received in step 808 are used to finalize travel arrangements and other resources through the services transaction system 806, and then again, completeness of responses is checked in step 809. Once all the arrangements have been completed, the meeting is finalized in step 810 and tickets are issued, etc. All of the specific arrangements would be sent to the attendees (via email, calendar insertions, etc.) for each sub-component of the meeting (e.g. each travel segment, the meeting itself, sub-meetings within the overall meeting, etc.).

Community Pricing

Figure 9:
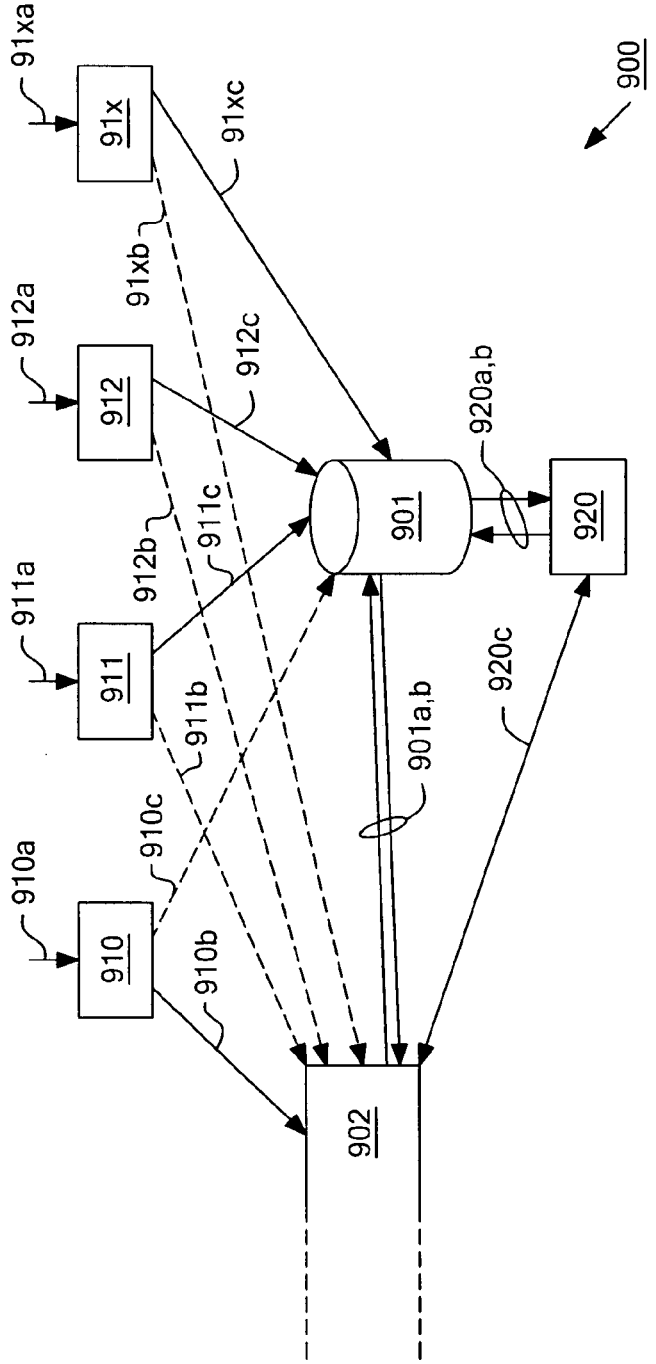
FIG. 9 illustrates a community pricing system, in accordance with one embodiment.

FIG. 9 shows a community pricing system 900, according to the novel art of the disclosure. A database 901 is used to maintain data about the various fees and surcharges charged by different providers for different services. The database 901 may contain data from several organizations, some of which may be shared, and some of which may not be shared. The information about those fees may be collected out of different interactions with service providers, such as interactions 910, 911, 912 and 91*x*. Those interactions are often made in conjunction with a services transaction system, such as the Talaris Services Platform 806. The fee data could be extracted, for example, from electronic publishing of fees (e.g., web-based) 910 by the supplier, from billings for services rendered 911, or from employees' expense reports 912, where an employee may be required to break out each fee and surcharge separately. A variety of possible additional modules 91X may be used to extract fee data from suppliers, corporations, and employees. An example of the data could be the corporation itself, by entering the specific costs for these components that the corporation has been able to negotiate. These rates would be "private" and only seen by employees of that specific corporation. And yet another source could be from individual employees. If travelers utilize a service from a specific supplier for which there is missing information, the system could survey them after the use of the service and ask them for pricing for specific components. For example, after a hotel stay, the system could ask if the user parked a car and if so, how much does it cost. Additionally, the system could gather information from any of the above mentioned sources on related services. For example, the system could gather information on how much a traveler paid for a taxi from a specific airport or hotel.

Further, in addition to gathering information on pricing of discrete items or services, information from the user community on the amenities in the hotel itself could be gathered. For example, information on whether there is a restaurant in the property and its price range, or whether the property has a van which they are willing to drive to and pickup from guests at local destinations, airports, etc. Also, the system could gather itemized details of services included in a "resort fee", as some hotels charge, and try to attach a value to those, based on a traveler profile. For example, such a resort fee may include local phone access, 800 numbers etc, but not high speed interne access, so it my be valuable only to travelers having a dial up modem and a service with local access etc. It is clear, that the number and combination of such bundles and benefits is great, but shall all be considered as part of a total cost analysis.

This data could be, for example, communicated in real time from a mobile device while an employee is checking in or requesting authorization for a service. Likewise, a response may also be provided in real time as to what is or is not an acceptable fee in accordance with organizational rules.

All these modules 910 through 91*x* may interact primarily with the services transaction system 806. In some cases the interaction may be through system 806 via connections 910*b*, 911*b*, 912*b*, and 91*xb* and then back to database 901 via connection 901*a*, or in other cases the modules may interact directly with database 901 via connections 910*c*, 911*c*, 912*c*, and 91*xc*. And in yet other cases the primary interaction may be with database 901, and with only secondary interactions with services transaction system 806. The raw data in 901 is then managed by community pricing manager 920.

Figure 10:
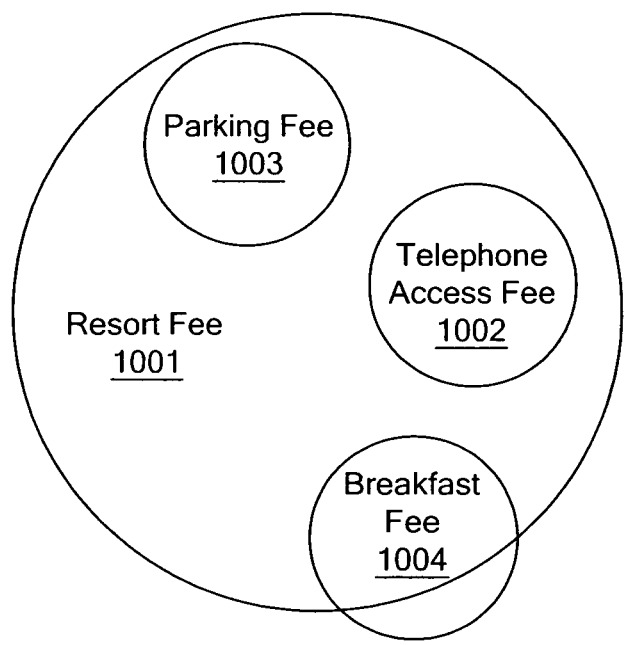
FIG. 10 illustrates example analysis of a hotel resort fee, in accordance with one embodiment.

In pricing manager 920, various analyses are made and may be used to extract and estimate the true cost of services to generate comparable pricing information for various providers. FIG. 10 shows an example analysis of a hotel resort fee 1001. Resort fee 1001 may contain, for example, the parking fee 1003 and the telephone access fee 1002, and it may or may not include a breakfast fee 1004. For some providers the organization may have negotiated the breakfast cost to be included, so that vouchers are given to the guests when they check in; whereas in other cases the breakfast may be a separate cost. Often parking, telephone and breakfast etc. can equal or even exceed the basic room cost at hotels.

The analysis of these different modules, where in some cases the parking fee is covered and in others not, allows a much more direct comparison of the true cost of services to members of an organization using specific services.

It is clear that many modifications and variations of this embodiment may be made by one skilled in the art without departing from the spirit of the novel art of this disclosure. It is clear that the services subject to the novel art of this disclosure are not limited to those provided by hotels. Other examples are airlines, which may have all kinds of surcharges, such as fuel, food, ticket change, and others. Other examples may include shipping, where additional fees may apply due to, for example, packaging costs or fees for dealing with an inaccurate address, to name just a few.

The processes described above can be stored in a memory of a computer system as a set of instructions to be executed. In addition, the instructions to perform the processes described above could alternatively be stored on other forms of machine-readable media, including magnetic and optical disks. For example, the processes described could be stored on machine-readable media, such as magnetic disks or optical disks, which are accessible via a disk drive (or computer-readable medium drive). Further, the instructions can be downloaded into a computing device over a data network in a form of compiled and linked version.

Alternatively, the logic to perform the processes as discussed above could be implemented in additional computer and/or machine readable media, such as discrete hardware components as large-scale integrated circuits (LSI's), application-specific integrated circuits (ASIC's), firmware such as electrically erasable programmable read-only memory (EEPROM's); and electrical, optical, acoustical and other forms of propagated signals (e.g., carrier waves, infrared signals, digital signals, etc.); etc.

Figure 11:
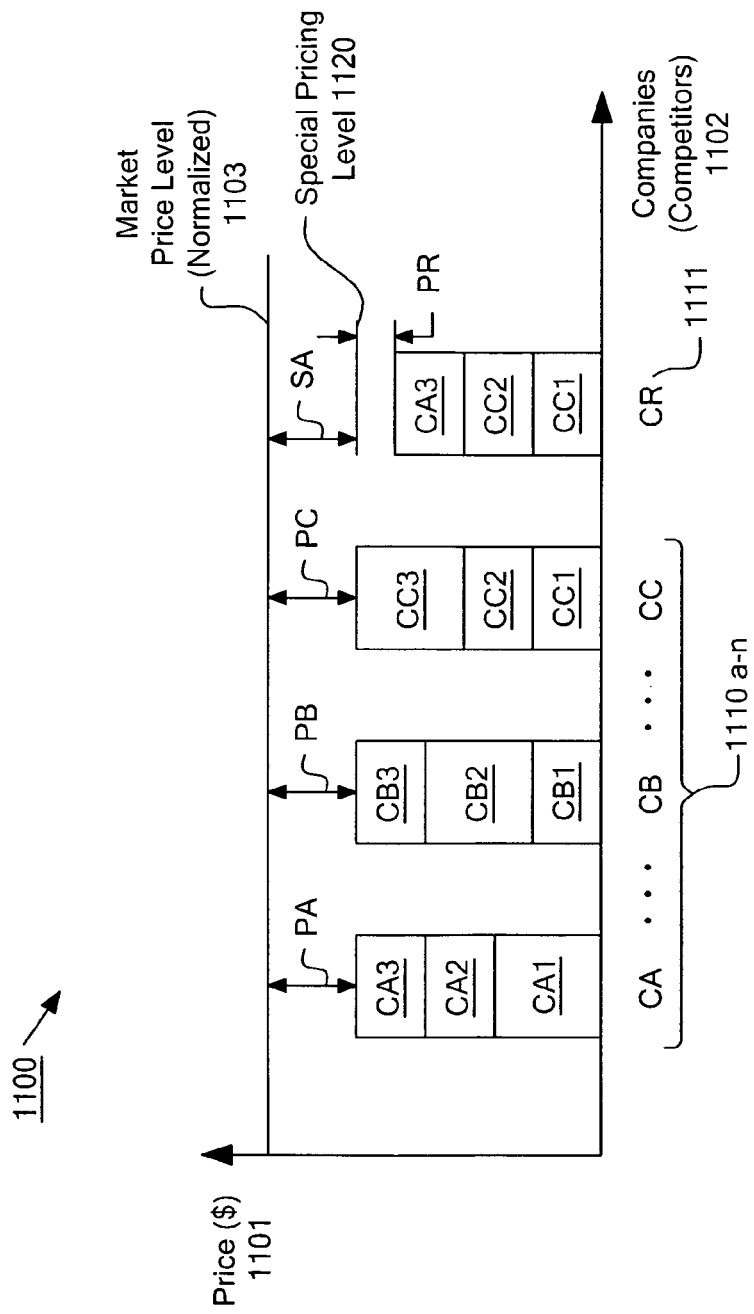
FIG. 11 shows an overview of exemplary cost structure model of several competing service providers.

FIG. 11 shows an overview of exemplary cost structure model 1100 of several competing service providers. On the horizontal axis are the competing providers 1102, with three specific competing service providers CA, CB, and CC 1110*a-n* shown. The y axis 1101 show the prices of their services in, for example, US dollars. For each of the competing providers CA, CB, and CB there are example cost structures CA1, CA2, CA3; CB1, CB2, CB3; and CC1, CC2, CC3, respectively, which in these abstract examples are the cost elements required to provide a service. The line 1103 at the top is the market price level, normalized for differences in service quality. Thus each competitor has a set of different cost structures CA1, CA2, CA3; CB1, CB2, CB3; and CC1, CC2, CC3, plus the profit margins PA, PB, and PC, which makes them reach the market price. Market price level 1103 may not be a straight line, because sometimes for various intangible reasons people are willing to pay more. Prices levels may also be affected by a branding issue, differences in size and quality, etc. Thus although all of these factors, when normalized, may result in a substantially flat line, individual price levels may vary.

An important element of the novel art of this disclosure is extracting from each of the cost models the lowest cost and thus creating a virtual competitor CR that offers a lower total cost. In FIG. 11 for example, CR is comprised of cost elements CC1, CC2, and CA3. Adding in a profit margin PR, such a model would result in cost savings SA without squeezing the profit margin of the service provider. This approach allows the provisioning system to achieve a special pricing level well below the normal market pricing, and the difference SA is direct savings to the organizations belonging to the provisioning system.

In the case of hotel rooms, for example, the cost components could be the costs of booking, cleaning, maintenance, amortization of investments (in furniture, equipment etc.), communications (phone, broadband Internet and TV), check-in and check-out, risk and amortization of purchase lease and/or market value of the property (adjustments for square footage of the rooms, for example, and location). Some of these cost components are a given, based on the property, but others can be changed by changing, for example, the communication equipment or service providers, or by subcontracting housekeeping, or by adjusting any of various other cost elements. By collecting as much information as possible through the service provisioning system, it can become clear where cost savings can be achieved, and by selecting a preferred partner, such cost saving ideas can be communicated to the partner without eliminating profit PR, resulting in the cost savings SA as shown in FIG. 11.

It is clear that the applications of this system are not limited just to hotel costs. For example, this approach may also apply to flight services, where there is the cost of the fuel (which ties into the fuel efficiency of the fleet), the cost for the amortization and depreciation of the fleet equipment, costs of onboard services, cost of booking tickets, cost for airport services, cost for baggage handling services, cost for maintenance of the airplane, etc.

One other aspect where costs can be modified is by moving the risk cost from the service provider to the provisioning system. For example, the provisioning system could buy large blocks of rooms from a hotel, thus removing the risk from the hotel (or other provider) and allowing the organization to resell unused inventory in the free market. Risk cost can be quite high, especially during slow travel periods. Currently, hotels try to manage risk by inviting seminars or similar events to fill up space. Similarly, airlines may offer reduced travel rates to promote the sale of empty seats.

Besides hotels and airlines, such cost models can apply to car rentals, to conferencing services, communication services, valet services, cleaning services, and many others.

Further, automated extraction of data as is available from offers, and actual billing can be used to augment and cross check data in the model for accuracy, etc.

It is clear that many modifications and variations of this embodiment may be made by one skilled in the art without departing from the spirit of the novel art of this disclosure.

Whereas many alterations and modifications of the present invention will no doubt become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of the claims which in them selves recite only those features regarded as essential to the invention.

The invention claimed is:

1. A system comprising:
   at least one server for:
   retrieving fee data from a database, wherein the fee data is from multiple service providers;
   automatically extracting costs components of a particular service from the fee data, the service provided by each of the multiple service providers, the extracted costs components different for each of the multiple service providers, at least one of the multiple service providers having a first profit margin in providing the service, wherein the service providers include air travel vendors and the costs components include one or more of costs of fuel, amortization of fleet equipment, onboard services, booking tickets, airport services, baggage handling, and maintenance of airplanes;
   comparatively cost analyzing the multiple service providers based only on the cost amounts of the extracted costs components of the multiple service providers;
   generating an updated costs model for the service based on the extracted costs components of the multiple service providers, wherein the updated costs model selectively combines the extracted costs components of the multiple service providers having lowest cost amounts and wherein the updated costs model produces a total cost for the service that is less than a total cost for the service provided by each of the multiple service providers;
   augmenting the updated costs model based on historical data regarding actual billing for the extracted costs components;
   cross checking the updated costs model based on the historical data regarding actual billing for the extracted costs components;
   setting a predetermined second profit margin based on the extracted cost components;
   communicating information about the extracted costs components of the multiple service providers having lowest cost amounts to a partner;
   allowing the partner to offer the service based on the information about the extracted costs components of the multiple service providers having lowest cost amounts while maintaining the second profit margin for the partner, the second profit margin being less than the first profit margin; and
   providing a cost savings to a purchaser of the service, from the partner and based on the information about the extracted cost components, in comparison to purchasing the service from each of the multiple service providers.

2. The system of claim 1, wherein the server is for allowing purchase of the service from at least one of the multiple service providers and resale of the service to remove risk from the at least one of the multiple service providers.

3. The system of claim 1, wherein each of the multiple service providers has a set of different costs structures associated with the service.

4. The system of claim 1, wherein the updated costs model includes a profit margin.

5. The system of claim 4, wherein the profit margin is at least equal to a lowest profit margin of the multiple service providers.

6. The system of claim 1, wherein the updated costs model is lower than all costs models offered by all of the service providers.

7. The system of claim 6, wherein the system is a provisioning system for the multiple service providers, to generate costs savings for the multiple service providers.

8. The system of claim 6, wherein service providers include hotel vendors and the costs components include one or more of costs of booking, cleaning, maintenance, amortization of furniture or equipment, communication equipment, and amortization of property value.

9. The system of claim 6, wherein service providers includes one or more car rental vendors, conferencing services, communication services, valet services, and cleaning services.

10. A computer implemented method comprising:
    retrieving, by a computing device, fee data from a database, wherein the fee data is from multiple service providers;
    automatically extracting, via the computing device, costs components of a particular service from the fee data, the service provided by each of the multiple service providers, the extracted cost components different for each of the multiple service providers, at least one of the multiple service providers having a first profit margin in providing the service, wherein the service providers include air travel vendors and the costs components include one or more of costs of fuel, amortization of fleet equipment, onboard services, booking tickets, airport services, baggage handling, and maintenance of airplanes;
    comparatively cost analyzing the multiple service providers based only on the cost amounts of the extracted costs components of the multiple service providers;
    generating an updated costs model for the service based on the extracted costs components of the multiple service providers, wherein the updated costs model selectively combines the extracted costs components of the multiple service providers having lowest cost amounts and wherein the updated costs model produces a total cost for the service that is less than total costs for the service provided by the multiple service providers;
    augmenting the updated costs model based on historical data regarding actual billing for the extracted costs components;
    cross checking the updated costs model based on the historical data regarding actual billing for the extracted costs components;
    setting a predetermined second profit margin based on the extracted cost components;
    communicating information about the extracted costs components of the multiple service providers having lowest cost amounts to a partner;
    allowing the partner to offer the service based on the information about the extracted costs components of the multiple service providers having lowest cost amounts while maintaining the second profit margin for the partner, the second profit margin being less than the first profit margin; and
    providing a cost savings to a purchaser of the service, from the partner and based on the information about the extracted cost components, in comparison to purchasing the service from each of the multiple service providers.

11. The method of claim 10, further comprising allowing purchase of the service from at least one of the multiple service providers and resale of the service to remove risk from the at least one of the multiple service providers.

12. The method of claim 10, wherein each of the multiple service providers has a set of different costs structures associated with the service.

13. The method of claim 10, wherein the updated costs model includes a profit margin.

14. The method of claim 13, wherein the profit margin is at least equal to a lowest profit margin of the multiple service providers.

15. A machine readable medium storing instructions, which when executed, cause a computing device to:
retrieve fee data from a database, wherein the fee data is from multiple service providers;
automatically extract costs components of a particular service from the fee data, the service provided by each of the multiple service providers, the extracted costs components different for each of the multiple service providers, at least one of the multiple service providers having a first profit margin in providing the service, wherein the service providers include air travel vendors and the costs components include one or more of costs of fuel, amortization of fleet equipment, onboard services, booking tickets, airport services, baggage handling, and maintenance of airplanes;
comparatively cost analyze the multiple service providers based only on the cost amounts of the extracted costs components of the multiple service providers;
generate an updated costs model for the service based on the extracted costs components of the multiple service providers, wherein the updated costs model selectively combines the extracted costs components of the multiple service providers having lowest cost amounts and wherein the updated costs model produces a total cost for the service that is less than total costs for the service provided by the multiple service providers;
augment the updated costs model based on historical data regarding actual billing for the extracted costs components;
cross check the updated costs model based on the historical data regarding actual billing for the extracted costs components;
set a predetermined second profit margin based on the extracted cost components;
communicate information about the extracted costs components of the multiple service providers having lowest cost amounts to a partner;
allow the partner to offer the service based on the information about the extracted costs components of the multiple service providers having lowest cost amounts while maintaining the second profit margin for the partner, the second profit margin being less than the first profit margin; and
provide a cost savings to a purchaser of the service, from the partner and based on the information about the extracted cost components, in comparison to purchasing the service from each of the multiple service providers.

16. The machine readable medium of claim 15, wherein the computing device comprises a provisioning system for the multiple service providers, to generate costs savings for the multiple service providers.

17. The machine readable medium of claim 15, wherein service providers include hotel vendors and the costs components include one or more of costs of booking, cleaning, maintenance, amortization of furniture or equipment, communication equipment, and amortization of property value.

18. The machine readable medium of claim 15, wherein service providers include air travel vendors and the costs components include one or more of costs of flight services, fuel, amortization of fleet equipment, onboard services, booking tickets, air port services, baggage handling, and maintenance of airplanes.

19. The machine readable medium of claim 15, wherein service providers includes one or more car rental vendors, conferencing services, communication services, valet services, and cleaning services.

20. The machine readable medium of claim 15, wherein the medium further stores instructions for causing the computing device to allow purchase of the service from at least one of the multiple service providers and resale of the service to remove risk from the at least one of the multiple service providers.

* * * * *